(12) United States Patent
Kenning

(10) Patent No.: US 9,157,879 B2
(45) Date of Patent: Oct. 13, 2015

(54) THERMALLY ACTIVATED MAGNETIC AND RESISTIVE AGING

(71) Applicant: Indiana University of Pennsylvania, Indiana, PA (US)

(72) Inventor: Gregory G. Kenning, Indiana, PA (US)

(73) Assignee: Indiana University of Pennsylvania, Indiana, PA (US)

( * ) Notice: Subject to any disclaimer, the term of this patent is extended or adjusted under 35 U.S.C. 154(b) by 0 days.

(21) Appl. No.: 14/249,478

(22) Filed: Apr. 10, 2014

(65) Prior Publication Data

US 2014/0292355 A1    Oct. 2, 2014

Related U.S. Application Data

(63) Continuation-in-part of application No. 13/446,579, filed on Apr. 13, 2012, now Pat. No. 9,041,419.

(60) Provisional application No. 61/476,044, filed on Apr. 15, 2011.

(51) Int. Cl.
*G01N 27/04* (2006.01)
*G01N 27/22* (2006.01)
*G01R 27/08* (2006.01)
(Continued)

(52) U.S. Cl.
CPC .............. *G01N 27/04* (2013.01); *B82Y 30/00* (2013.01); *B82Y 40/00* (2013.01); *G01N 27/02* (2013.01); *G01N 33/02* (2013.01)

(58) Field of Classification Search
CPC ........ G01R 27/08; G01R 27/22; G01R 31/06; G01N 27/00; G01N 27/04; G01N 27/06

USPC ........ 324/601, 654, 691, 693, 71.1, 541, 543, 324/545–547; 422/90, 82.02, 50, 68.1, 422/82.01, 83, 88, 62, 82; 250/221, 222.2
See application file for complete search history.

(56) References Cited

U.S. PATENT DOCUMENTS 4,949,039 A    8/1990   Grunberg
5,057,434 A   10/1991   Prusik et al.
(Continued)

FOREIGN PATENT DOCUMENTS

EP    0443260 A1    8/1991

OTHER PUBLICATIONS

G.G. Kenning, J. Bowen, P. Sibani, G.F. Rodriguez, "Temperature Dependence of Fluctuation Time Scales in Spin Glasses," Phys. Rev. B, 2010.

(Continued)

*Primary Examiner* — Tung X Nguyen
*Assistant Examiner* — Neel Shah
(74) *Attorney, Agent, or Firm* — Gifford, Krass, Sprinkle, Anderson & Citkowski, P.C.

(57) ABSTRACT

Examples of the present invention include apparatus and methods for monitoring aging of an item. A solid-state structure is located within, adjacent to, or otherwise proximate the item, the solid-state structure including nanostructures. The electrical resistance and/or magnetization of the solid-state structure is determined to determine the degree of aging of the item. In representative examples, the solid-state structure includes nanostructures of a metal, such as a ferromagnetic metal, within a non-magnetic matrix, such as a semimetal, semiconductor, or insulator.

17 Claims, 14 Drawing Sheets

(51) Int. Cl.
  *G01R 31/06* (2006.01)
  *B82Y 30/00* (2011.01)
  *B82Y 40/00* (2011.01)
  *G01N 27/02* (2006.01)
  *G01N 33/02* (2006.01)

(56) References Cited

U.S. PATENT DOCUMENTS

| | | | |
|---|---|---|---|
| 5,064,605 | A | 11/1991 | Ruddy et al. |
| 5,201,583 | A | 4/1993 | Lai et al. |
| 5,932,813 | A | 8/1999 | Swartzel et al. |
| 6,617,963 | B1 | 9/2003 | Watters et al. |
| 6,642,016 | B1 | 11/2003 | Sjoholm et al. |
| 7,492,164 | B2 * | 2/2009 | Hanhikorpi et al. .......... 324/633 |
| 7,537,384 | B2 | 5/2009 | Hilgers |
| 7,612,325 | B1 * | 11/2009 | Watkins et al. ............ 250/222.2 |
| 7,714,593 | B2 * | 5/2010 | Varpula et al. ................ 324/654 |
| 7,719,404 | B2 | 5/2010 | Makela et al. |
| 7,898,833 | B2 | 3/2011 | Prejbeanu et al. |
| 8,217,669 | B1 * | 7/2012 | Watkins, Jr. .................. 324/693 |
| 2007/0166831 | A1 | 7/2007 | Watkins et al. |
| 2007/0176773 | A1 * | 8/2007 | Smolander et al. ...... 340/539.26 |
| 2008/0150556 | A1 * | 6/2008 | Han et al. ...................... 324/693 |
| 2009/0087348 | A1 | 4/2009 | Claus et al. |
| 2009/0165533 | A1 | 7/2009 | Han et al. |
| 2010/0068749 | A1 | 3/2010 | Bauer et al. |
| 2010/0109645 | A1 | 5/2010 | Park et al. |
| 2011/0003279 | A1 | 1/2011 | Patel |

OTHER PUBLICATIONS

H. Park, M. Pleimling, "Aging in coarsening diluted ferromagnets," Phys. Rev. B82, 144406 (2010).

P.R. Rios, F. Siciliano Jr., H.R. Zschommler Sandim, R.L. Plaut, A.F. Padilha, "Nucleation and Growth During Recrystallization," Materials Research, vol. 8, No. 3, 225-238, 2005.

M. Sachan, C. Bonnoit, S.A. Majetich, Y. Ijiri, P.O. Mensah-Bonsu, J.A. Borchers, and J.J. Rhyne, "Field evolution of magnetic correlation lengths in Î-Co nanoparticle assemblies," Applied Physics Letters 92, 152503 (2008).

Y. Jun, J. Seo, J. Cheon, "Nanoscaling Laws of Magnetic Nanoparticles and Their Applicabilities in Biomedical Sciences," Accounts of Chemical Research, vol. 41, No. 2, 179-189, Feb. 2008.

Supplementary European Search Report from co-pending application Serial No. EP12770711, issued Aug. 13, 2014.

* cited by examiner

Field (T)

THERMALLY ACTIVATED MAGNETIC AND RESISTIVE AGING

CROSS-REFERENCE TO RELATED APPLICATIONS

This application is a continuation-in-part (CIP) of U.S. patent application Ser. No. 13/446,579 filed Apr. 13, 2012, which in turn claims priority to U.S. Provisional Application 61/476,044 filed Apr. 15, 2011, both of which are incorporated herein by reference.

FIELD OF THE INVENTION

Examples of the invention relate to methods and apparatus for monitoring aging processes, for example using a solid-state apparatus.

BACKGROUND OF THE INVENTION

Aging processes are significant in many commercial activities, including handling of perishable items such as food and medicine, part lifetimes in engineering applications, process control, and the like. A typical approach is to determine an end-of-life date as a fixed time period from the initial manufacture. However, this fails to account for variations in temperature or other ambient conditions during the lifetime.

Hence, there is a need for improved methods and apparatus allowing monitoring of aging processes in a variety of applications.

SUMMARY OF THE INVENTION

Examples of the present invention include apparatus and methods for monitoring aging, for example in a monitored item such as a physical system. An example apparatus includes a solid-state sensor material which has a physical property that varies as a function of both time and temperature. In examples, the physical property may be electrical resistance, magnetoresistance, or magnetization. An example may include a solid-state composite structure including nanoparticles of a first material, for example a ferromagnetic material such as a ferromagnetic metal. The nanoparticles may be spherical nanoparticles, nanorods, nanoflakes, and the like. The matrix material preferably has a physical property, such as electrical resistivity, appreciably different from the ferromagnetic material. In some examples, the solid-state structure may include alternating layers of a nanostructured material, such as a metal, and a matrix material.

Typically, the physical property changes faster with time as the temperature increases. Hence, aging properties of items can be evaluated in a more accurate manner than using a simple timing mechanism. For example, in some aspects, a solid-state structure used as an aging sensor has an electrical resistance (or resistivity) that changes as a function of both time and temperature, providing an indication of aging in an associated item.

In some examples, nanoparticles, such as nanoflakes, of a first material, such as a ferromagnetic material, are supported within a matrix, such as a semi-metal or semiconducting matrix. Preferably, the matrix material has an electrical conductivity significantly less than the nanoparticle material. In some examples, morphological changes occur within the sensor material, causing an appreciable change in electrical conductivity. Nanostructures may melt and interact with each other to form nanowires of the first material within the matrix material. The electrical conductivity falls appreciably as nanowire networks form through the matrix material, and this may be detected using a pair electrodes. Morphological changes may reduce the magnetization of the solid-state material, which can be detected using a GMR (giant magnetoresistance) sensor.

In some examples, the first material may be a metal, such as a ferromagnetic metal. The matrix material may be a metal, semimetal, semiconductor, or insulator. Morphological changes in nanostructures of the first material reduce the electrical resistance of the solid-state structure, due to at least partial melting of the first material and formation of nanowires of the first material, during aging.

The melting of nanostructures of the first material, such as ferromagnetic nanoflakes, and the formation of nanowires thereof may result from an interaction between the nanoparticles, and this may be facilitated by magnetic interactions between proximate ferromagnetic nanostructures, such as nanoparticles.

A method of monitoring aging of an item comprises locating a solid-state structure proximate the item, for example adjacent the item, within or on the item packaging, or otherwise located so that the sensor and the item experience similar or correlated temperatures as a function of time. For example, an aging sensor may be placed on a food package, on a supporting shelf, or in the same room.

An example aging sensor includes a solid-state structure having nanostructures of a first material, such as a ferromagnetic material, distributed in a non-ferromagnetic matrix material. A physical parameter of the solid-state structure (such as electrical resistance, magnetization, or in some cases magnetoresistance) is determined at intervals. The physical parameter varies with both time and temperature of the solid-state structure, allowing the effects of both to be used to determine when aging has reached a threshold level (for example, related to food spoilage, chemical process completion, or other desirable or undesirable aging process).

A physical parameter is determined relative to an initial value of the physical parameter, for example as a ratio of the current value physical parameter and the initial value, and used to determine the aging of the item. Hence, advantageously, both time and temperature variations are used in the determination of aging.

In some examples, physical parameter varies due to morphological changes of the nanostructures within the solid-state structure, such as melting of nanostructures such as ferromagnetic nanoflakes. In some examples, nanoflakes of cobalt, iron, manganese, nickel, or a ferromagnetic rare earth metal are formed within a semimetal matrix, including arsenic, antimony, tin, or bismuth, alloys thereof, or other semimetallic material. In some examples, the matrix material may be a semiconductor, such as a semiconducting polymer.

In some examples, electrical resistance decreases as the item ages, and this decrease may be determined using an electronic circuit, either combined with the solid-state structure in a unitary device, or as a separate circuit that can be electrically connected to the aging sensor. For example, electrical resistance changes may be detected by an electronic circuit. In some examples, an electronic circuit including a GMR sensor may be used to monitor changes in magnetization of the solid-state structure.

An alert, such as a visual or audible alert, may be provided if aging has reached a predetermined threshold. A monitored item may be food item, medical item, chemical compound such as pharmaceutical or industrial process chemical, reaction vessel, other chemical or biological process, or a mechanical component.

An example apparatus for monitoring a degree of aging of an item includes a solid-state structure including nanostructures of a first material, such as a ferromagnetic material, distributed in a (non-ferromagnetic) matrix material, the solid-state structure having a physical parameter, the physical parameter being an electrical resistance or a magnetization, where the physical parameter decreases with time, and the rate of decrease increases with an increase in ambient temperature (within an operational temperature range, and during the useful lifetime of the device).

An example solid-state structure includes nanostructures of a first material, such as a ferromagnetic material, distributed through a non-ferromagnetic matrix material, may be enclosed in a housing. The non-ferromagnetic matrix material has an electrical resistivity appreciably greater than that of the ferromagnetic material, so that an electrical resistance measured between first and second electrodes, in electrical contact with the solid-state structure, falls as the morphology of the nanostructures changes, for example through the formation of nanowires of the first material.

In a representative process for forming a sensor, a matrix material (such as a metal, semi-metal, semiconductor, or dielectric matrix material) and first material (such as a ferromagnetic material) are alternately deposited on a substrate. The resulting structure may be termed a multilayer structure, however this may simplify the actual structure as discussed in more details later. For example, the first material may self-assemble into nanostructures. For example, a solid-state (nominally) multilayer structure may have the form substrate/ matrix layer/first material layer/matrix layer. The number of first material layers may be from, for example, 1 to 100 layers.

The first material may be ferromagnetic material, and may be a ferromagnetic metal such as cobalt, iron, manganese, alloys thereof, and the like. A preferred ferromagnetic metal is cobalt.

The matrix material preferably has an electrical conductivity appreciably less than the ferromagnet, and may for example be a semi-metal such as arsenic, antimony, bismuth, tin, and the like. In some examples, the matrix material may be a semiconductor. In some examples, the matrix material may be an insulating material such as a dielectric material.

In further examples, an array of ferromagnetic nanoparticles are supported within a matrix material, and magnetic interactions between neighboring nanoparticles result in temperature and time dependent magnetoresistance and magnetization. Changes in physical properties may be due to an electronic effect. An example device includes an array of ferromagnetic nanoparticles dispersed through a nonferromagnetic matrix. RKKY electronic interactions between proximate nanoparticles cause spin flipping of the ferromagnetic state and hence modifications in electrical conductivity. A magnetoresistance effect may be observed, and this effect may be reversible using a strong magnetic field to reset and reuse the aging sensor.

An improved method of fabricating an aging sensor includes depositing alternating layers of a first material and a matrix material on a substrate, the first material forming self-assembled nanostructures between matrix layers. The nanostructures in each layer of the solid-state structure formed then melt into each other during operation of the example aging sensor, providing a reduced electrical conductivity path through the structure.

Examples of the invention relate to monitoring a physical property (e.g. electrical resistance or magnetization) of a solid-state device to measure of the aging of an associated item (such as a physical or other system). Example devices include a magnetic multilayer structure, and structures including magnetic nanoparticles. Examples include solid-state structures, such as multilayer structures, that show aging properties as a function of time and temperature. Aging may be observed as appreciable changes in the magnetization and/or resistance of the device as a function of time.

A characteristic time can be associated with one or more decay processes, for example in magnetization and/or electrical resistance of the sensor material. An example sensor may be configured to operate as clock, or a switch that, at a particular time (dependent on the temperature), switches off or on. A multilayer structure can be configured to give a desired characteristic time, and characteristic times may be in the range of seconds, hours, days, weeks, or other desired range.

Monitored items may include food products (including beverages), chemicals such as pharmaceuticals, mechanical components, and the like.

One embodiment of the instant invention is an RFID food item aging apparatus that includes a solid-state structure having a plurality of nanostructures of a first material distributed in a matrix of a second material. In addition, the solid-state structure has a first measurable value of electrical resistance, magnetization, and/or capacitance at a first time and a second measurable value of electrical resistance, magnetization, and/ or capacitance at a second time. The second measurable value is a function of a temperature profile of the solid-state structure between the first time and the second time. The RFID food item aging apparatus also has an antenna in communication with the solid-state structure, the antenna being operable to broadcast at least one of the first measurable value and the second measurable value to an RFID reader.

The solid-state structure can have a first morphological shape at the first time and a second morphological shape at the second time. The first morphological shape can include at least one layer of the plurality of nanostructures between layers of the matrix material. In addition, the plurality of nanostructures have a first physical size when the solid-state structure has the first morphological shape and a second physical size when the solid-state structure has the second morphological shape. It is appreciated that the second physical size can be greater or larger than the first physical size. In addition, the plurality of nanostructures having the first physical size can be a plurality of single magnetic domain nanostructures. Stated differently, each of the plurality of nanostructures can have a physical size that contains a single magnetic domain.

The plurality of nanostructures grow from the first physical size to the second physical size by at least one of diffusion between the plurality of nanostructures and melting of at least a portion of the plurality of nanostructures. In some instances, the first physical size is in the form of elliptical-shaped nanoparticles and the second physical size is in the form of nanowires.

A pair of electrodes in electrical contact with the solid-state structure can be included and the pair of electrodes are configured to determine or aid in measuring the first measurable value and the second measurable value. In some instances, the pair of electrodes are configured to measure the first and second measurable values parallel to the layers of the solid-state structure, while in other instances the pair of electrodes are configured to determine the first and second measurable values perpendicular to the layers of the solid-state structure.

In the event that the first and second measurable values are first and second resistance values, the second resistance value is less than the first resistance value due to a metal-non-metal (MNM) transition of the matrix material from the semiconductor side, i.e. the matrix transitions from acting like or having semiconductor properties to acting like or having metal properties. In addition, the MNM transition of the matrix can be a function of reduced local magnetization of the plurality of nanostructures that have the second physical size which is larger than the first physical size. It is appreciated that the reduction in magnetization can be due to the growth of nanoparticles which are originally single magnetic domain in size when they have the first physical size, but become multiple magnetic domain in size when they have the second physical size.

In some instances, the first and second measurable values are first and second capacitance values. In such instances, the solid-state structure can be a resistor that is part of an inductance-capacitance-resistor (LCR) circuit. The LCR circuit with the multilayer structure can be a stand-alone radiofrequency time-temperature indicator. In addition, the LCR circuit can be a series LCR circuit, or in the alternative a parallel LCR circuit.

The solid-state structure can take advantage of capacitive anomalies of the matrix material undergoing the MNM transition. In particular, the capacitance can increase rapidly when the temperature of the matrix material approaches the MNM transition from the semiconductor side. In particular, the increase in capacitance demonstrated by the solid-state structure can be coupled to or within an LCR circuit as part of a stand-alone radio frequency time temperature indicator (RFTTI). Monitoring signals that monitor the age of the food item can include the resonant frequency, the signal amplitude, and the phase difference between in-phase and out-of-phase responses. Stated differently, one or more resonant circuits that include the solid-state structure disclosed herein can be used as part of an RFID food item aging apparatus.

DETAILED DESCRIPTION OF THE INVENTION

Figure 1:
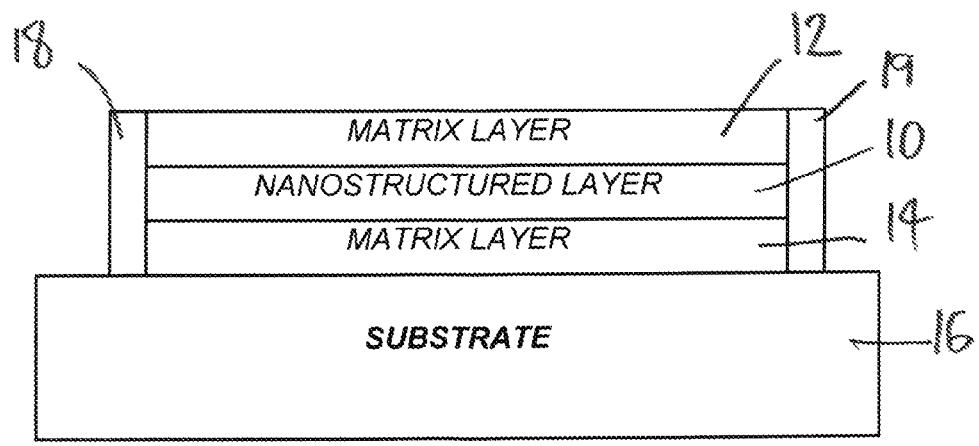
FIG. 1 is a simplified schematic of a multilayer sensor.

Examples of the present invention include apparatus and methods for monitoring aging in a monitored item (e.g. a physical system), using magnetic and/or resistive aging of a nanoparticle system. Examples include a solid-state structure including nanostructures of a first material distributed in a matrix material, in some examples as a multilayer structure including layers of nanostructures and layers of a matrix material. Some examples include ferromagnetic nanostructures (such as nanoparticles) within a semi-metal matrix material.

Appreciable magnetization (in particular, for ferromagnetic nanostructures) and electrical resistance decays may be observed, and a characteristic time determined. The characteristic time is strongly temperature dependent, so that the magnetization and resistance decrease as a function of both time and temperature. Further, the characteristic time may be controlled using deposition properties. Hence, the characteristic time can be predetermined to correlate with the aging processes in a monitored item.

Examples of the present invention include the use of magnetization and/or resistance aging decays in magnetic multilayer structures to characterize the aging of a system under test. Example magnetic multilayers include Co/Sb multilayer systems.

In experimental observations, aging was characterized by a large decay in both the magnetization (80% decay in some examples) and the resistivity (40% decay in some examples). A characteristic time can be assigned to the decay curves, for example as a point of inflection or as the time for a predetermined fall in the measured physical parameter.

In ferromagnetic/semimetal solid-state structures, resistivity did not require an applied magnetic field to decay and to first order is field independent. These data suggest that both the initial pre-aged are nominally super ferromagnetic and final post-aged samples are possibly super ferromagnetic. Analysis indicates aging is caused by thermally induced fluctuations in single magnetic domain Co nanoparticles and their interaction with the magnetic and electronic environment.

Examples of the present invention include an electronic device configured for aging monitoring. At a given temperature, this material acts like a clock and a switch. The accuracy of the clock is dependent on experimental variations in fluctuations in the $\tau_t$ timescale, which can be improved using modified techniques of nanoparticle deposition and characterization. This type of clock and switch might be useful in epidermal drug delivery or as a more accurate indicator of the age of perishable chemicals or foods, and the like.

Experimental time parameters were observed in timescales ranging from seconds to minutes to hours to days to weeks. The temperatures at which these timescales are observed ranged from just below room temperature all the way up to about 120° C. However, these observed values are not limiting.

Magnetic and resistive aging were observed in self-assembled nanoparticle systems produced in a multilayer Co/Sb sandwich. The aging decays are characterized by an initial slow decay followed by a more rapid decay in both the magnetization and resistance. The decays are large accounting for almost 70% of the magnetization and almost 40% of the resistance for samples deposited at 35° C. For samples deposited at 50° C. the magnetization decay accounts for ≈50% of the magnetization and 40% of the resistance. During the more rapid part of the decay, the slope of the decay changes sign and this inflection point can be used to provide a characteristic time. The characteristic time is strongly and systematically temperature dependent, ranging from ≈100 s at 400K to ≈300,000 s at 320K in samples deposited at 35° C. Samples deposited at 50° C. displayed a 7-8 fold increase in the characteristic time (compared to the 35° C. samples) for a given aging temperature, indicating that this timescale is tunable. Both the temperature scale and time scales are in potentially useful regimes.

Pre-aging, scanning tunneling microscopy (STM) revealed that the Co forms in nanoscale flakes. During aging, the nanoflakes melt and migrate into each other in an anisotropic fashion forming elongated Co nanowires. This aging behavior occurs within a confined environment of the enveloping Sb layers. The relationship between the characteristic time and aging temperature fits an Arrhenius law indicating activated dynamics.

Examples of the present invention include methods and apparatus related to thermally activated magnetic and magnetoresistive aging, including applications at ambient temperatures and a wide variety of useful timescales. Producing this functionality in a solid-state device offers many advantages, including miniaturization, integration with electronic devices, reduced cost, and improved control. It is possible to quantitatively attach a value of the material property to a particular system age. A large change in a physical component such as the magnetization or in particular the resistance can be used as a switch. As a detectable change occurs at a given time for a particular temperature, applications include uses as a clock. At a given temperature, these material act like a clock which at a particular time effectively flips a switch.

The temperature dependence of the magnetic and electrical response provides an improved set of aging criteria, compared with a simple elapsed time. In this respect, the hotter the temperature, the faster the material ages, and the faster the switch is thrown. This is useful as a more accurate indicator of the age of chemicals, foods, etc., and allows improved expiration dates to be determined compared with approaches that stamp a date without product monitoring.

In representative examples, the time-dependent magnetization and resistivity of a Co/Sb multilayer were evaluated, as a function of deposition time and annealing time.

FIG. 1 is a highly simplified schematic of a multilayer structure, in which a matrix layer 14 is deposited on substrate 16, a nanostructured layer (in some examples, of a ferromagnetic material) is then deposited on the matrix layer, and a second matrix layer is deposited on the ferromagnetic layer. The number of layers may vary from 2 to 100. In representative examples, the matrix material is a semi-metal layer, and the nanostructured layer is a ferromagnetic metal such as cobalt. First and second electrodes shown schematically at opposed ends of the multilayer structure (18, 19) may be used to monitor electrical resistance, either in a direction parallel to the layer planes (as shown) or perpendicular to layers. In the later case, an electrode layer may be located between the first matrix layer (14) and the substrate (16), and a second electrode formed on the topmost exposed matrix layer (12 in FIG. 1, though a solid-state structure may include many more nanostructured/matrix alternating layers.)

The nanostructured layer may comprise nanostructures of a metal that self-assembles into discrete nanostructures when deposited on the matrix layer 14, for example due to surface self-assembly of a first material. During aging processes, the nanostructures may partially melt, and form a conducting pathway between the electrodes. If the matrix material conductivity is significantly less than the nanostructured material, for example at least one order of magnitude less at an operating temperature, the formation of physical interconnections such as nanowires between formerly discrete nanostructures causes the conductivity to fall. (Here, conductivity refers to the electrical conductivity).

Figure 2:
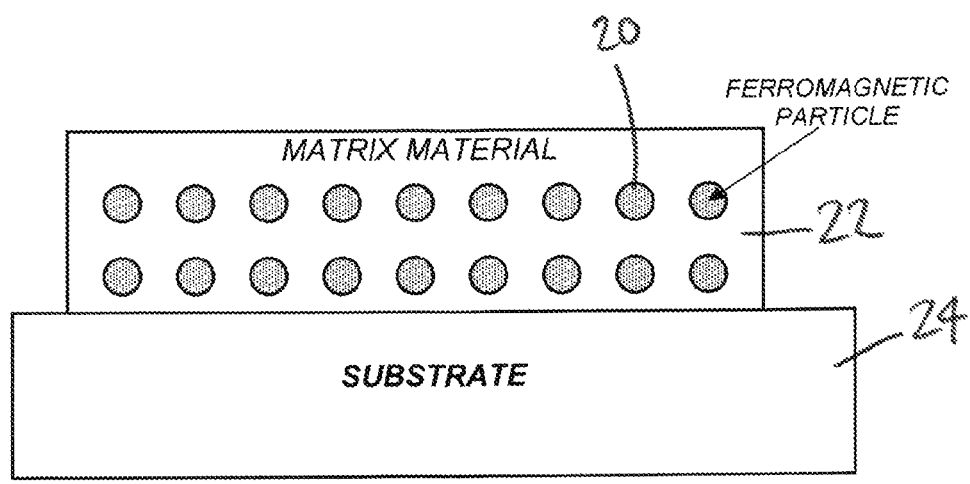
FIG. 2 is a schematic of an array of ferromagnetic particles within a matrix.

FIG. 2 is a simplified schematic whereby ferromagnetic particles 20 are dispersed through a matrix. The structure is supported by a substrate 24. The properties of this configuration will be discussed in more detail later on in the specification.

Experimental examples described below used cobalt as the ferromagnetic metal and antimony (Sb) as a semi-metal matrix. However these are exemplary and other ferromagnetic metals and matrix materials may be used. Any appropriate matrix material may be used, such as silicon or alumina ($Al_2O_3$), or in some examples flexible substrates such as metal foils and polymers.

Experimental examples were fabricated in which Sb was a semi-metal matrix layer, and Co was used as a nanostructured ferromagnetic metal layer. FIG. 1 apparently simplifies the multilayer solid-state structure considerably, as discussed later in relation to STM observations. In discussing layer thicknesses, the nominal layer thickness corresponds to that which would be obtained for a uniform layer thickness. In practice, the ferromagnetic metal tended to aggregate and form nanostructures in the form of nanoscale flakes within the matrix material. The thickness of these nanoflakes may exceed the approximate layer thickness estimated from the amount of deposited material, due to plumping of the material. Nominal layer thicknesses may be in the range 0.5 nanometers to 10 nanometers.

The ferromagnetic metal may form self-assembled nanoparticles within the structure. STM observations revealed that some particles may be 4 nanometers thick, for a nominal 1.5 nanometer layer thickness. This is evidence of surface self-assembly of the cobalt layer on the antimony layer.

Other matrix materials may be used, such as other semi-metals including tin and bismuth, or other semiconductors or insulator. In some examples the matrix layer need not be a semi-metal layer, and may in some cases have a resistance that is much higher than the ferromagnetic metal. This allows greater resistance changes to be obtained.

In experimental fabrication examples, Sb and Co were alternately deposited on a silicon substrate. The Sb layer covered the substrate quite well as discussed in more detail later, and observations of the cobalt layer deposited on Sb showed that the cobalt tended to grow into each other right away by a self-assembly mechanism. The aging process in these experiments appeared to be a morphological change, by which magnetic attractions between the ferromagnetic cobalt particles induced melting together of nanoflakes and formation of nanowires. Electrical conductivity is better through cobalt nanowires than through the matrix material, so that resistivity decreases.

In some examples, the ferromagnetic metal nanoparticles flow together, and may push away intervening matrix material.

Figure 3:
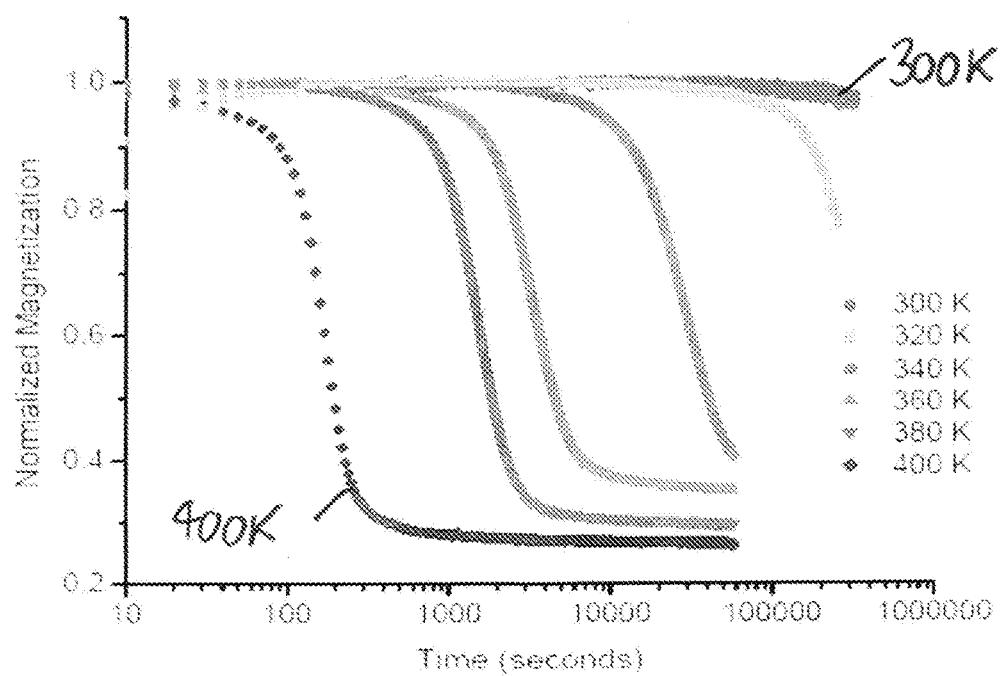
FIG. 3 shows normalized magnetization as a function of time and temperature for an antimony/cobalt (Sb/Co) multilayer structure.

FIG. 3 shows variation in the normalized magnetization as a function of time. The figure shows normalized magnetization decay curves for temperatures ranging from 320 K to 400 K, for samples deposited at 335K on the 111 face of Si and with curves normalized to their maximum value. The figure shows that the magnetization decay is large, and may account for 70% of the magnetization. The inflection point of the decaying portion may be used to define a characteristic time, $\tau_i$.

The characteristic time is highly sensitive to the deposition temperature of the magnetic multilayer. Hence, aging sensors can be fabricated for a wide variety of applications, and the characteristic time may be selected according to the aging process of the monitored physical system.

The nominal layer thickness of the monitored multilayer was Co/Sb 1.5 nanometers/2.5 nanometers. Aging decays in samples with 10 layers, 50 layers, and 100 layers were analyzed and showed similar effects. The characteristic time was estimated to be approximately 3 weeks for samples deposited at 35° C., and approximately 6 months for samples deposited at 50° C., for storage at room temperature. When not in use, samples were stored at liquid nitrogen temperature to avoid aging occurring.

FIGS. 4A-4D show the effect of deposition and annealing time on the resistance changes in a magnetic multilayer. The figures show normalized resistance decay curves ($R/R_{max}$) measured in a magnetic field of 0.01 T for temperatures from 320 K to 400 K, for samples deposited at 335K on the 111 face of Si with curves normalized to their maximum value. R represents the resistance at a certain degree of aging (a function of time and temperature, as shown), and $R_{max}$ is the resistance of an initial state before significant aging processes. An electronic circuit can be used to provide an alert (e.g. visual and/or audible) when the normalized resistance falls to a predetermined value).

Figure 4A:
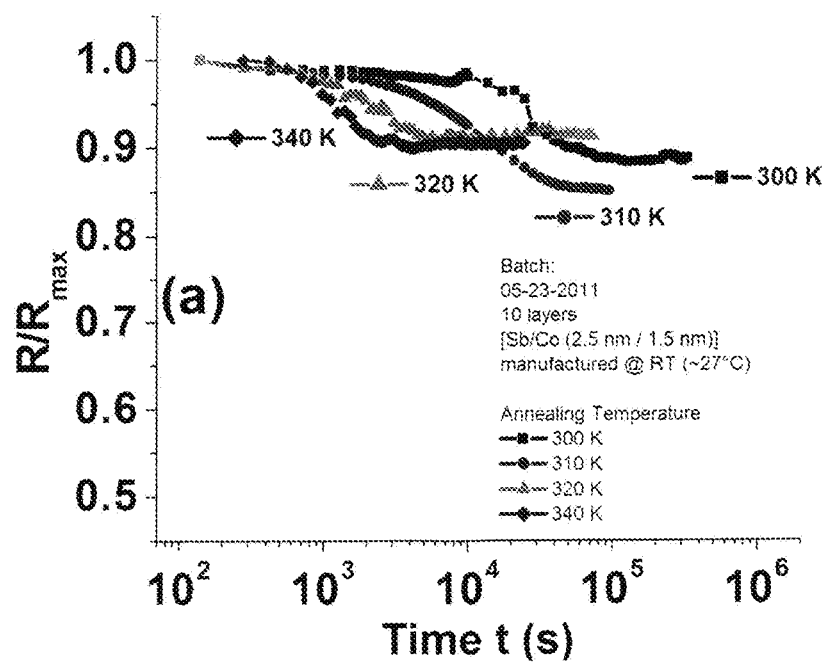
FIGS. 4A-4D show electrical resistance changes as a function of deposition temperature and annealing temperatures, for a Sb/Co multilayer structure.

FIG. 4A shows samples manufactured at near room temperatures (27° C.) and subsequently annealed at 300, 310, 320, and 340 Kelvin (K). For room temperature deposition, little resistance change was observed.

Figure 4B:
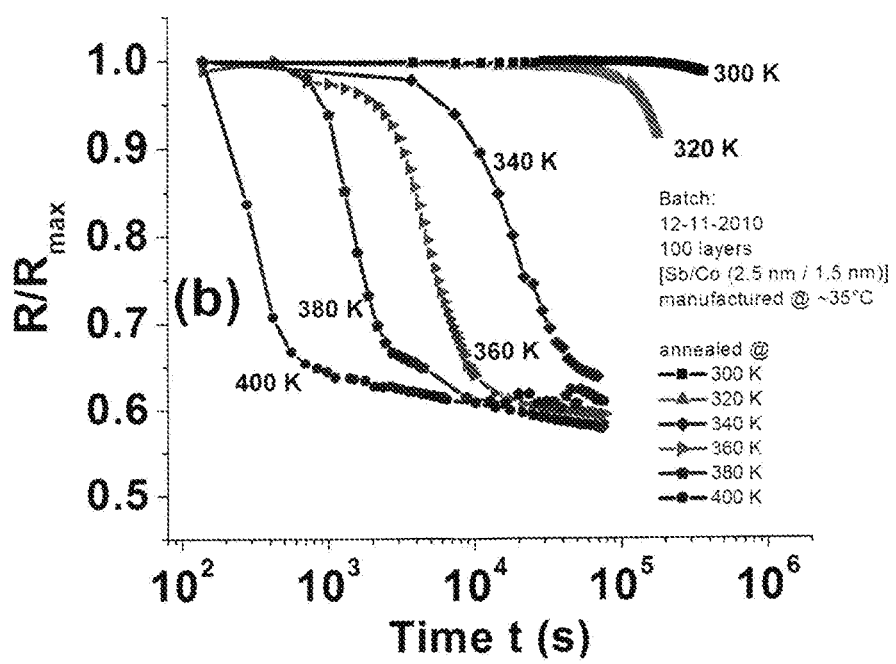

FIG. 4B shows results obtained for a sample manufactured at 35° C. This figure shows that these samples can show appreciable electrical resistivity changes, in some cases over 40%, and the figure further shows that the characteristic time may be adjusted by an annealing step to the desired time. For comparison, FIGS. 3 and 4B display aging decay curves for the magnetization and normalized resistance (respectively) as a function of temperature for samples deposited at 35° C. An external magnetic field of 0.01 T was applied during both of these measurements.

Figure 4C:
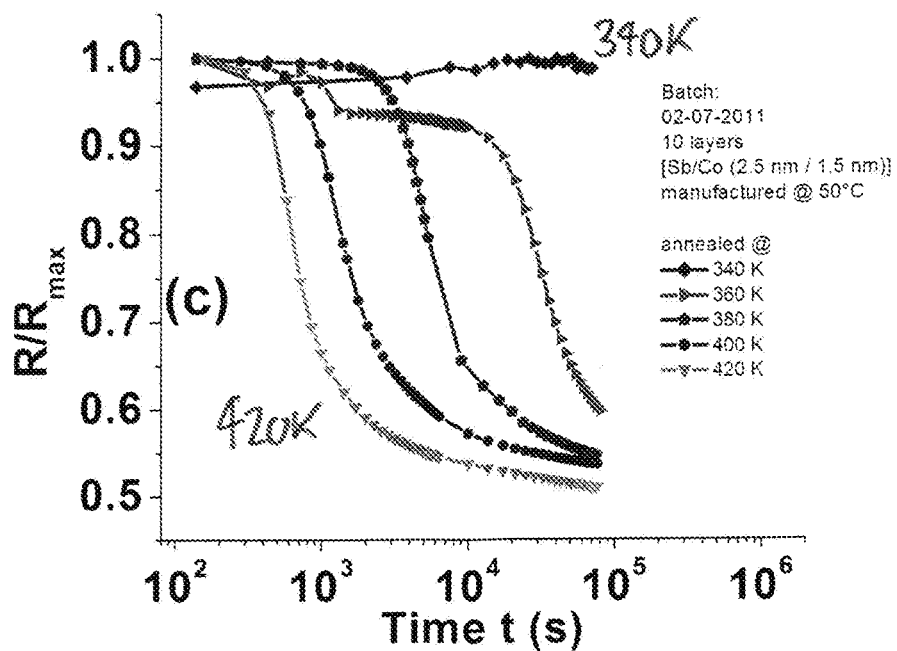

FIG. 4C shows electrical resistivity changes for a magnetic multilayer manufactured at 50° C. Again, a subsequent annealing step has considerable effect on the resultant behavior. The higher the annealing temperature, the shorter the characteristic time. The annealing step used temperatures of 340 Kelvin-420 Kelvin at 20K intervals.

Figure 4D:
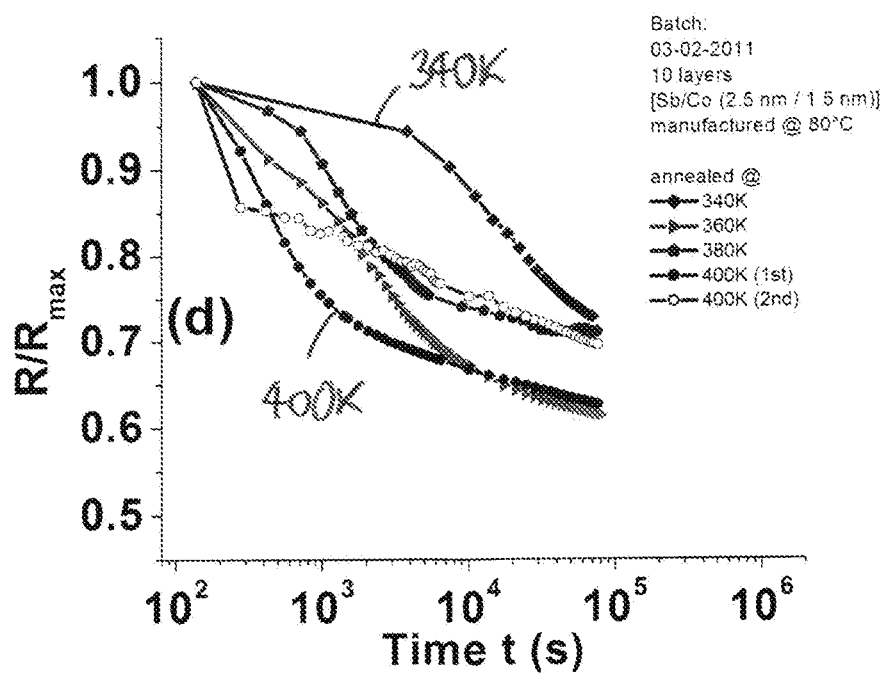

FIG. 4D shows a sample fabricated at 80° C., with annealing at different temperatures. In this case performance was relatively poor, compared to FIG. 4C, but still may be usable.

In aging experiments, the aging decays may be characterized by two timescales. The first time scale represents birth or the beginning of aging while the second time scale represents how fast the system ages. For these experiments, we set the birth timescale (t=0 s) to the time when the sample was placed in the preheated cryostat, the field turned on and the measuring program initiated. The inflection point of the decay curves, as observed on the logarithmic scale, provides a second timescale that quantifies the rate of aging. For both the magnetization and resistance this time is denoted $\tau_i$. At this time the function $S(t)=dA(t)/d\ln(t)$ (where A(t) is the decaying signal) produces a maximum. Both the magnetization and resistance (at 0.01 T) of the Co/Sb system undergoes an aging decay which shifts significantly as a function of temperature. For a sample deposited at 35° C. the magnetization curves undergo a total decay of approximately 60-80% of the initial magnetization. Every increase of 20K brings a ≈5-10 fold increase in $\tau_i$. The resistance displays a decay of approximately 40% of the initial resistance.

FIGS. 5A-5F show a hysteresis study of a Co/Sb multilayer. A sample was deposited at 350K on the 111 face of Si and aging performed at 400K monitored, where hysteresis curves labeled A-B-C-D correspond to time points along the aging curve of FIG. 5D.

These figures show an experimental analysis of hysteresis loops taken at various times during the aging decay process. Experimental analysis of the hysteresis loops of states taken at various times through from the pre-aged and post-aged states shed insight on possible mechanisms for the magnetization decays.

Results were obtained for a single Co/Sb sample fabricated at 50° C. on the 111 face of silicon. Aging was performed at 400 K. In this description, unless otherwise indicated, deposition temperatures are given in Celsius and aging temperatures given in degrees Kelvin. The as-assembled magnetization decay of FIG. 5D was measured in a magnetic field of 0.01 Tesla and the indicated points A, B, C and D indicate the points where the corresponding hysteresis points were taken at 300 K. For example, the curve of FIG. 5A was obtained at point A shown in FIG. 5D. The hysteresis loops of unaged samples have a ferromagnetic signature with a coercive field of approximately 0.006 Tesla. The unaged sample (FIG. 5A) also has a remanent magnetization of approximately 1.1 memu.

While the coercive field remains similar in the aged samples, the remanent magnetization decreases to 0.8 memu and the slope in the high field magnetization increases. These changes may be indicative of a possible paramagnetic or frustrated contribution. After aging well past the rapid decay phase and into the slower and possibly logarithmic decay, the in-plane hysteresis again shows ferromagnetism with a reduced saturation moment. The out-of-plane magnetization, which displayed a ferromagnetic behavior before aging, has a somewhat noisy paramagnetic signature after aging. It is possible that there is significant demagnetization in the out-of-plane data.

The results showed a total magnetization decay of approximately 50% of the maximum magnetization while the total resistance decay was close to 40% of the maximum. The sample was aged at 400 K for set periods of time and the magnetization decay measured. After aging, the sample was removed from the cryostat to room temperature. The cryostat was then cooled to 300 K and the sample placed back in the cryostat for the hysteresis measurements at 300K.

Figure 5A:
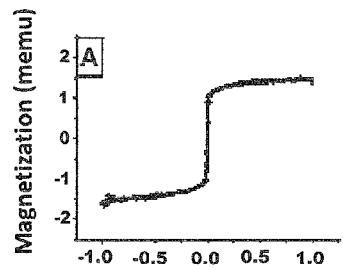
FIGS. 5A-5F show a magnetic hysteresis study of a single magnetic multilayer.
Figure 5B:
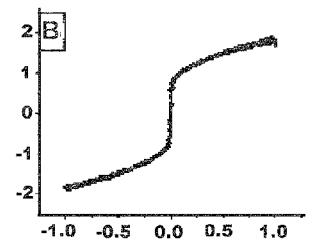

During hysteresis measurements the sample would often be held at 300K for up to 12 hours. At 300K the estimated characteristic time is on the order of six months aging would be slow enough to ignore the effects due to aging during the hysteresis measurements. This retardation in time scale is evident in FIG. 5D, where the segments making up the set of decays measured at 400K are reconstructed into a single decay. The hysteresis loops of the pre-aged samples have a ferromagnetic signature with the coercive field of approximately 0.006 T. The unaged sample also has a remanent magnetization of 1.1 emu and a slight increasing slope in the high field regime. At 1 T the magnetization reaches a maximum of approximately 1.4 emu. After aging at 400K for 600s, changes in the hysteresis loops were immediately observed (FIG. 5B). While the coercive field remains similar to the unaged sample there is a distinct tilt to the hysteresis loop, the remanent magnetization decreases to 0.8 emu and the slope in the high field magnetization increases. These changes are indicative of a possible paramagnetic or frustrated contribution. Both of these effects are accentuated with further aging.

Figure 5C:
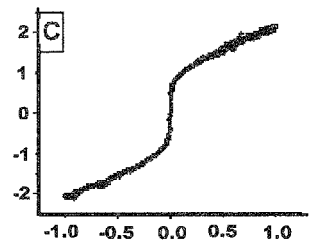
Figure 5D:
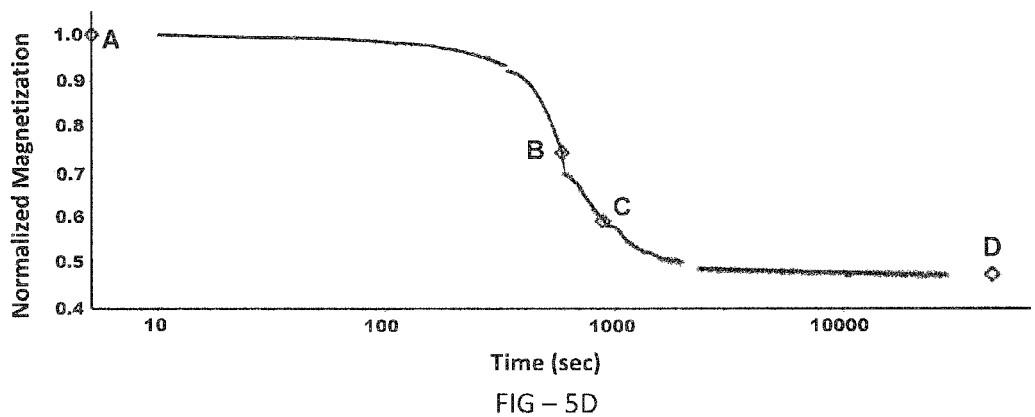
Figure 5E:
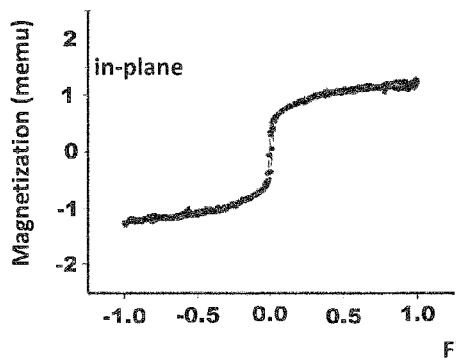
Figure 5F:
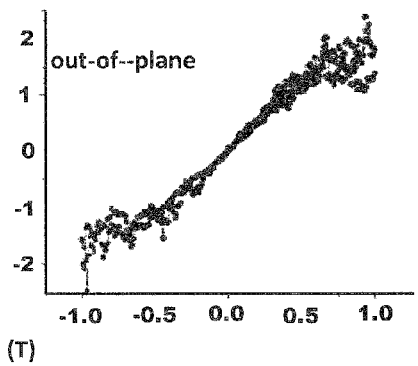

FIGS. 5B and 5C are taken during the rapid decrease in the magnetization. This data also lends credence to the argument that the decrease in the magnetization is not due to loss of moment through chemical bonding to O, Si or even the Sb. Chemical bonding would reduce the saturation moment and we would expect that the net moment (nominal saturation magnetization) in high field would decrease. After aging well past the rapid decay and well into a much slower, possibly logarithmic decay, the in-plan hysteresis again shows ferromagnetism with a reduced saturation moment. The out-of-plane magnetization, which showed a ferromagnetic behavior before aging interestingly, in this sample, has a paramagnetic signature after aging.

One explanation is that before aging the nanoflakes behave as single magnetic domain ferromagnetic particles. As the samples age, these flakes begin to melt, flow, and contact each other. As nanowires form, the enhanced size increases the demagnetizing field, possibly inducing anti-parallel alignment of magnetic domains and the formation of magnetic domain walls. This is a probable mechanism for reducing magnetization during aging.

In the initial stages of nanoflake contact, the energy of a magnetic domain wall is minimized if it forms at the smaller contact interface as opposed to in the interior of the particle. Also, the c axis of nanoflakes is likely misaligned in the initial contact, possibly leading to frustration between moments. This may cause the tilting of the hysteresis loops during the aging process.

Figure 6:
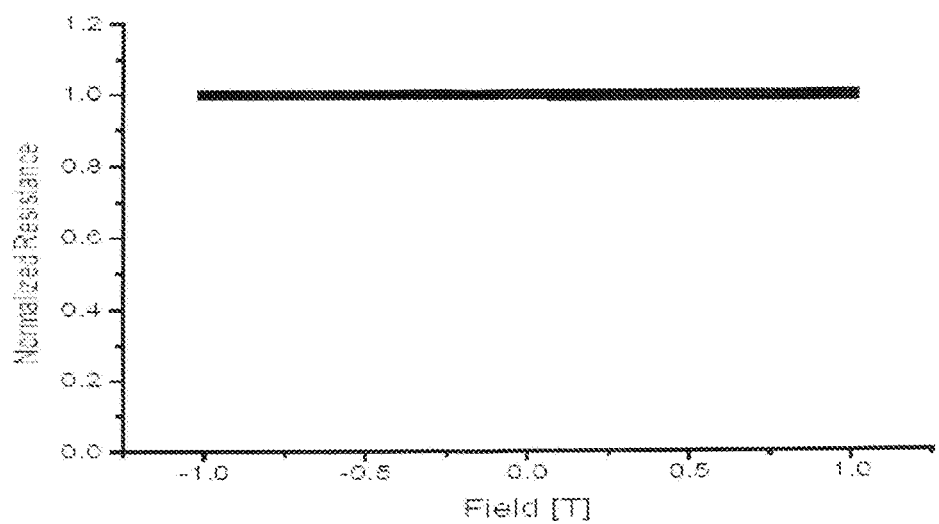
FIG. 6 shows magnetic field independent magnetoresistance for a Co/Sb multilayer, indicating that a resistive effect is observed, rather than a magnetoresistive effect.

FIG. 6 shows the normalized resistance as a function of external magnetic field. This figure shows that the resistive effects observed in this magnetic multilayer are not magnetoresistance effects. Even though a magnetic/metallic multilayer may appear to be a GMR system, it is not reacting to an external field as one. Even though the majority of the resistance decay measurements reported here were made in 0.01 T, to remain consistent with the magnetization measurements, similar decays were observed in zero magnetic field. Therefore the response is a resistive effect, not a magnetoresistive effect.

Figures 7A, 7B, 7C:
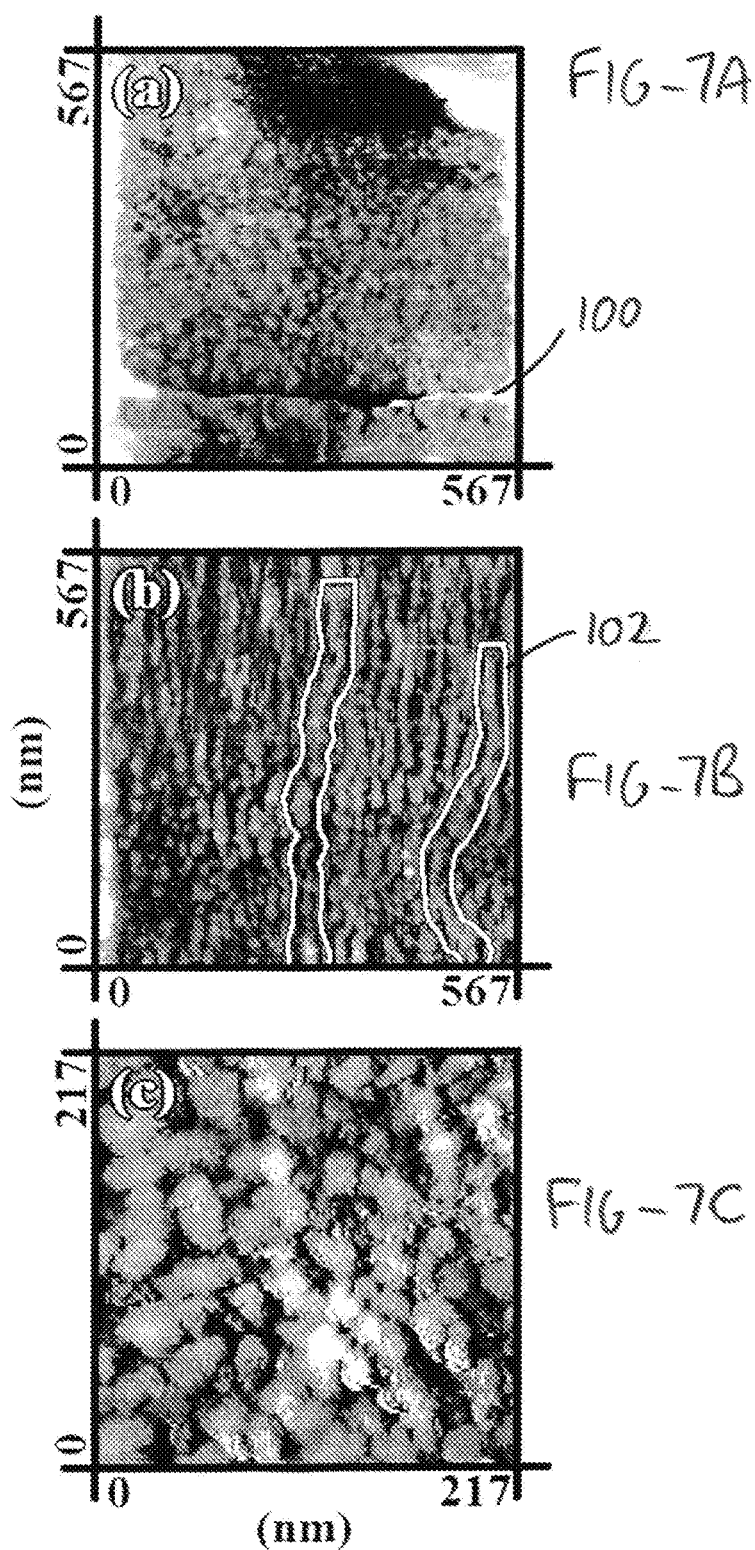
FIGS. 7A-7C are further images of the effect of aging on the magnetic multilayer.

FIGS. 7A-7C show STM images. FIG. 7A is an STM image of a pre-aged Sb/Co/Sb magnetic multilayer. The Sb layers were nominally 2.5 nanometers thick, and the Co layer was 1.5 nanometers thick. As the Sb layer thickness increases, electrical resistance of the solid-state structure increases. As the Co layer thickness increases, the time scale may increase. In this context, pre-aged means before aging processes are significant.

FIG. 7A shows the Sb layer on a silicon substrate, and shows a microcrack 100 near the bottom of the sample. However, this was atypical and microcracks were not generally observed so that dislocations are unlikely to be a source of the electrical resistivity changes. The images show the microcrack 100 near the bottom of the image, and a film edge on the right-hand side. The Sb layer wets the surface of the substrate and provides a generally uniform coverage. The Co particles appear to be observable through the upper Sb layer.

FIG. 7B shows an STM image of the same sample after aging, after which the cobalt layer has changed morphology. A comparison of FIGS. 7A and 7B, which are from the same sample, shows that the results of aging are directly observable. FIG. 7B is the same sample but a different area as that shown in FIG. 7A, after being heated to 400K for 20 minutes. This is approximately the same time as required for fully aging, i.e. full decay of the fast decaying portion of the magnetization and resistance curves. There are dramatic morphological differences. The Co layer has crept anisotropically through the Sb layer, forming long nanowires 102. These nanowires provide an improved conductivity path through the nanostructured layer.

Examples of the present invention also include improved methods of forming nanowires, for example through the melting and physical interconnection of nanostructures in a nanostructure/matrix multilayer solid-state structure, and improved nanowires formed by this process. Semiconductor devices using quantum size effects for modified electrical or optical properties may be fabricated using this approach.

Statistical analysis of the nanowires determined a mean width of 15 nanometers and lengths from 100 nanometers up to 570 nanometers. The maximum length measurements were limited to image size. The nanowires had a mean length of 330 nanometers with a standard deviation of 130 nanometers, the nanowire thickness being approximately 2.3 nanometers. Apparently, there was significant overlap between the nanowires along both their lengths and widths, and they may be in electrical contact. The directionality of the wires is observable but not presently understood.

Analysis of the Co particles suggested a Gaussian distribution of sizes, with a mean maximum length of 19 nanometers and a standard deviation of 5 nanometers. The nearest neighbor distribution was estimated as a mean distance of 4.0 nanometers with a standard deviation of 1.7 nanometers. Profile analysis indicates that the Co particles were on average 2.5 nanometers in height. The lateral dimensions are much larger than the thickness, and the particles are effectively nanoflakes. The Co attains approximately 50-70% coverage. The nanoflakes were self-assembling and had a large surface-to-volume ratio.

FIG. 7C shows an Sb/Co single bilayer system, where Co is the top layer deposited at 50° C. The sample was removed from the deposition chamber and stored for a period at 77 Kelvin, to prevent aging, and then studied at room temperature after warming up for 2 hours. The image shows nanoparticles approximately 30 nanometers in size and 1.6 nanometers in thickness, producing 91% coverage and apparently overlapping. The aging process appears isotropic, and in this case, apparently, the Sb layer confined the nanoparticles, slowing down migration and producing the time-dependent effects.

Figure 8A:
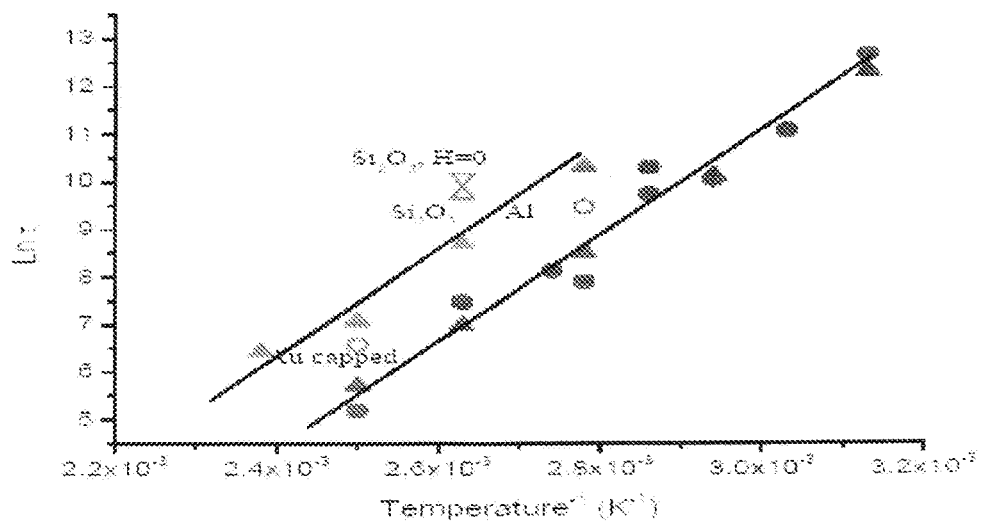
FIGS. 8A and 8B illustrate activated dynamics analysis of the aging process.
Figure 8B:
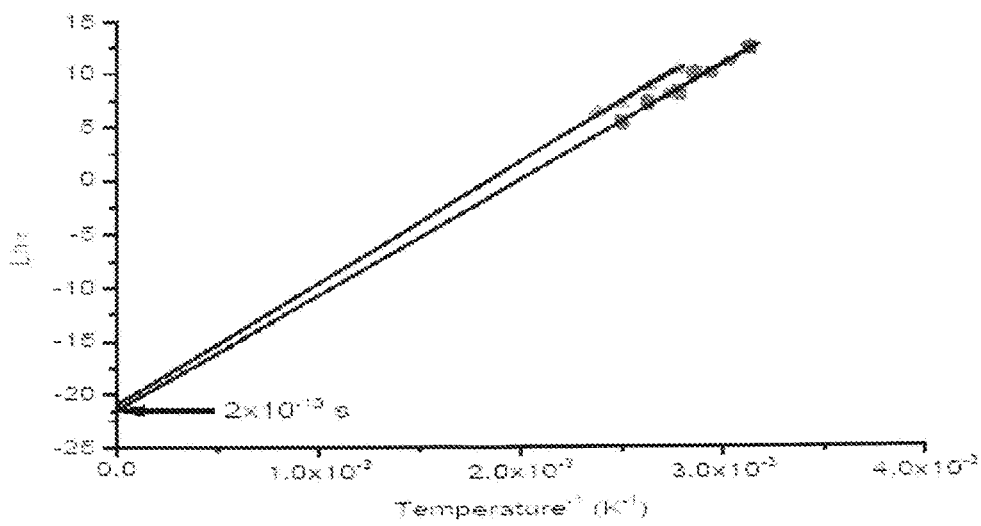

FIGS. 8A and 8B show an activated dynamics analysis of the aging process. FIG. 8A shows the natural log of the characteristic time against reciprocal temperature. The data is shown for two samples deposited at 35° C. and 50° C., the characteristic time being determined from the inflection point of the decay curves. FIG. 8A shows $\ln \tau_i$ vs. $1/T$ for all samples measured, where (unless indicated) all samples were deposited on the 111 face of Si and measured in a field of 0.01 T. The lower line indicates samples deposited at 35° C., and the upper line indicates samples deposited at 50° C. Circles are $\tau_i$ determined from magnetization data, triangles are $\tau_i$ values determined from resistance data.

FIG. 8B shows ln $\tau_i$ vs. 1/T for all samples measured in this report. Unless indicated, all samples were deposited on the 111 face of Si and measured in a field of 0.01 T. The lower line indicates samples deposited at 35° C., and the upper line indicates samples deposited at 50° C. Circles are $\tau_i$ determined from magnetization data, triangles are $\tau_i$ values determined from resistance data. Characteristic times were obtained from both magnetization and resistance decays. This figure shows how characteristic time is controllable by adjusting the deposition parameters. For the sample deposited at 35° C. the activation energy was determined to be 0.91 eV.

Figure 9A:
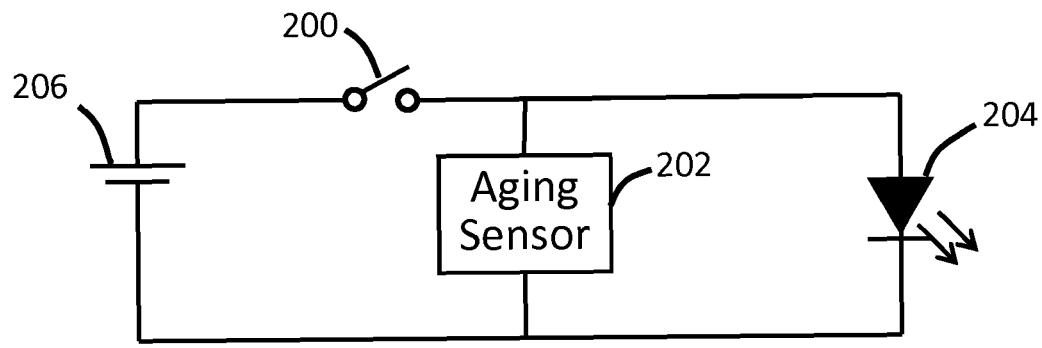
FIGS. 9A-9C illustrate possible electronic circuits including an aging sensor.
Figure 9B:
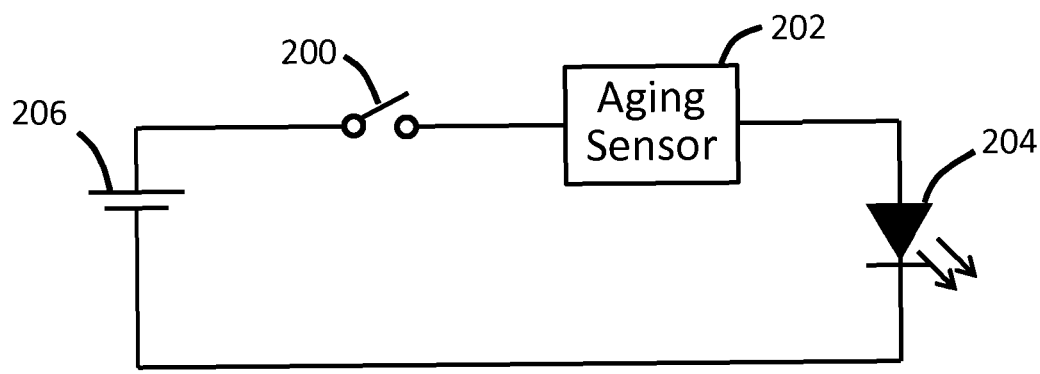

FIGS. 9A-9B show example electronic circuits including a battery 206, switch 200, sensor 202, and light emitting diode (LED) 204. An LED may have an associated current-limiting series resistor (not shown for clarity). In FIG. 9A, the LED illuminates when the switch is closed, as long as the resistance of the sensor 202 has not fallen enough so that it provides an alternative current path. FIG. 9B shows a series configuration, where a fall in resistance due to aging may cause the LED to light. These circuits can be configured so that the light turns on or off as an aging threshold is reached. The effect may use an internal battery as shown, other dedicated power supply, or in some cases may use an external source of power. In some examples, an electronic circuit includes a GMR sensor, which is responsive to magnetization changes in a proximate aging sensor. The resistance changes of a GMR sensor may be detected in an analogous manner to the electrical resistance changes of an aging sensor.

Figure 9C:
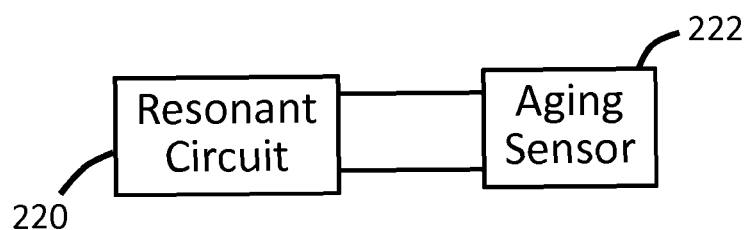

FIG. 9C shows a simplified schematic allowing modification of resonant circuit 220 using sensor 222, whereby capacitive or inductively-coupled transponders may be used to provide a characteristic frequency which changes as the resistance of the sensor changes. In some cases, wireless interrogation of the transponder may be used, for example by using the sensor to switch a reactive or resistive component out of the resonant circuit. In other examples, conventional analog circuits (such as operational amplifier circuits) can be used to determine when a threshold degree of aging has occurred.

An example sensor includes a sensor material and electrodes configured to make electrical contact with the sensor material, such as a solid-state structure as described herein. For example, a sensor material may be formed as a strip, with electrical contacts at each end of the strip. The strip of sensor material may be formed on a substrate, which may be adhered to a surface close to the item to be monitored. The sensor material may be enclosed in a housing, having terminals in electrical contact with the electrical contacts. In a multilayer structure, the electrical resistance changes may be detected in a direction parallel to the layer planes (as in the experimental examples discussed above.) In other examples, electrodes may be configured to detect electrical resistance changes perpendicular to the layer planes. The solid-state structure may be supported by a substrate. Aging-correlated electrical resistance changes were observed using silicon (Si), alumina (Al2O3), and plastic (Mylar) substrates. Hence, in some examples, the substrate may be a rigid planar substrate such as a dielectric substrate. In some examples, the substrate may be a flexible polymer substrate. An adhesive layer (for example, on the opposite side of the substrate from the solid-state structure) may be provided to adhere the sensor to an item for aging monitoring of the item.

Discussion of Experimental Data

The time and temperature dependence of the decays in these samples indicate that the process may be thermally activated. In nature when a system in one state can transition to another state by a thermally activated hoping over an energy barrier to another state the system can generally be described by an Arrhenius law. The Arrhenius law, as written for chemical dynamics, determines a frequency of transition between states at temperature T. This law was generalized by Neel to the Neel-Arrhenius form to describe the characteristic spin flip time (barrier hopping time) of superparamagnetic nanoparticles:

$$\tau = \tau_o \exp(E_a/k_b T) \quad (1)$$

In this equation, $E_a$ is the activation energy or barrier height, $\tau_o$ is the fluctuation timescale and $\tau$ is the characteristic hopping time at temperature T. In the case of superparamagnetic particles, $E_a$=KV where K is the anisotropy constant and V the particle volume.

A second and more likely scenario, considering the change in morphology, is thermally activated melting of the nanoflakes. Nanoparticle melting is a known effect and can be a nuisance when it comes to producing electronic contacts. The large surface to volume ratio of these flakes should strongly enhance melting. The nucleation and growth of crystallites during annealing is discussed in Rios et al., Mat. Res., 8(3) (2005).

The STM images suggest that one and likely two growth mechanisms are present. The nanoflakes are apparently migrating through the intervening Sb to couple to each other. The model for the velocity of the interface of high angle boundaries is thermally activated. Driving and retarding forces to this mechanism have also been considered. Second, once the Co crystals form an interface, the process of coalescing can reduce the free energy by including a rotation of the crystal axis of one of the particles to form a single crystal. Also, the main driver or cause for the reduction in free energy can be the formation of magnetic domain walls between coalescing magnetic nanoparticles. While both of these mechanisms have been applied to annealing of polycrystalline samples it is likely that they can also be applied to the Co/Sb system.

Plotting ln$\tau_i$ vs. 1/T for two sets of samples deposited at 35° C. and 500° C. Samples deposited at 35° C. include sets of $\tau$i values from both magnetization and magnetoresistance decays. It can be observed that both sets of data are compatible. Fluctuations in $\tau_i$ data provide a better metric of the reproducibility of time scales then say the error in the determination of $\tau_i$, which are generally small. It would appear that, within the constraints of the percolation limit and smaller nanoparticle fluctuation time scales, that a range of characteristic time scales may be achieved, at a single temperature, by depositing the samples at different temperatures. FIG. 3B is the same plot 1 as FIG. 3A but with the fit extrapolated to T→0. This extrapolation gives the value of $\tau_o$, the thermal fluctuation timescale. The value of $\tau_o$ obtained for fits over samples from the two deposition temperatures is approximately 1-4×10$^{-10}$. This is consistent with timescales obtained from magnetic susceptibility data for single magnetic domain Ni. From the graph of sample deposited at 35° C., an activation energy of 0.91 eV is found.

The measured resistivity of the pre-aged sample is approximately one order of magnitude greater than what we would expect from a calculation of the expected resistance of this particular multilayer sandwich. FIG. 7A shows a microcrack near the bottom of the sample. A sample with large numbers of dislocations or a fractured sample could produce a large resistivity but as previously mentioned, the number of cracks observed was minimal, and surface profiling suggests that the Sb forms a contiguous layer, so it is unlikely that dislocations are the reason for this enhanced resistance.

Two effects may contribute to raise the resistance of the Co nanoflakes to the flow of conduction electrons. In a normal metal, current is carried equally by both electrons of both spin components. In a ferromagnetic, current is carried preferentially by the majority spin component. At a ferromagnetic/non-ferromagnetic metal interface, this mismatch produces an electrochemical mismatch that increases the boundary resistance. Spin orbit scattering off of the interface is also likely to contribute to the resistivity. Upon the advent of aging, the nanoparticles begin to flow into each other. An electron needs to only cross one interface to enter the extended low resistivity cobalt nanowires where it can be transported with little resistance for hundreds of nanometers. This is likely the short-circuit which decreases the resistance.

There are many mechanisms that can cause a decrease in the magnetization. The hysteresis measurements as well as the STM data provide clues as to the magnetization decrease during aging. First, the preaged samples look ferromagnetic. While super ferromagnetism is a possibility magnetization vs. temperature studies down to 10K, show no evidence of the ultra small paramagnetic particles forming between the nanoparticles during the deposition as observed in CoFe/$Al_2O_3$. As a matter of fact the saturation magnetization can be fit to the standard $T^{3/2}$ form between 10K and 300K. The STM results indicate nanoparticles that are extended in-plane (~15-25 nm) while the out of plane thickness is only ~3-4 nm. The in-plane magnetization is more than three time greater than the out of plane magnetization. This geometry significantly decreases the demagnetizing field, stabilizing the particle against magnetic domain wall formation. Therefore, it is likely that the nanoflakes behave as single magnetic domain ferromagnetic particles. As the samples age these flakes begin to come in contact with each other. As the nanowires begin to form it is likely that the enhanced sizes will increase the demagnetizing field and the magnetic domain walls will form.

In the initial stages of nanoflake contact two factors must be considered. First, in the in initial contact the energy of a magnetic domain wall would be minimized if it formed at the much smaller contact interface as opposed to in the interior of a particle. Second, the c-axis of the individual nano flakes are likely misaligned in the initial contact which may lead to frustration between the moments. It is likely that this frustration is the cause of the tilting of the hysteresis loops during aging. The out-of-plane paramagnetic signature observed in the heavily aged sample is interesting and suggests that $Sb_3Co$ may be forming at the nanowires interface.

Sample fluctuations may also influence the accuracy of time dependent data. A time dependent decay may be used in various applications as a clock and a switch. However, the experimental fluctuations in $\tau_i$ reduces accuracy of timing applications. The e-beam evaporator used effectively produces a point source of evaporating atoms and the substrates were laid out in a plane bisecting the sphere of that source. Sample to sample deviations are therefore to be somewhat expected. Variations in nanoflake sizes and separation distances also likely contribute to inhomogeneities in the time scale. There are a variety of techniques available for controlling sample sizes (Majetich et al., "Magnetostatic Interactions in Magnetic Nanoparticle Assemblies: Energy, Time, and Length Scales," J. Phys. D, 39, R407-R422, 2006), and separations (Jun et al., Accounts of Chemical Research, 41(2), 179189, 2008) in spherical nanoparticles which may be modified for use with examples of the present invention.

Further Discussion of Sample Preparation and Handling

The samples used in the study were deposited in a vacuum of $\leq 1 \times 10^{-6}$ Torr in an Edwards model 2033 e-beam evaporator. The deposition rate was monitored in situ during the entire course of the deposition with a deposition monitor. Deposition rates were approximately 0.2-0.3 nm/minute. The majority of the samples discussed herein were produced through deposition on the <111> face of silicon, although data is reported for a few samples deposited on $Al_2O_3$, as well as deposited on common commercial aluminum foil. As the Edwards evaporator has a single e-beam gun, multilayer samples were produced by evaporating the Sb and then rotating the Sb 99.999% target out of the gun and the Co 99.9% into the gun to produce a layer of cobalt. Co nanoparticles were produced in the solid-state within a metallic environment. Co is known to form magnetic nanoparticles in a variety of environments and has a bulk resistivity of 62.7 nΩ·m at 300 K.

Bulk Co has a melting temperature of 1,495° C. Sb is a semimetal and has a bulk resistivity (417 nΩ·m) almost seven times higher that of Co. Bulk Sb has a melting temperature of 630.74° C. We waited approximately 5 minutes after the Co was deposited in order to maximize time for possible Volmer-Weber particle growth mechanisms to act. Samples were made with nominal layering of Co/Sb 1.5 nm/2.5 nm. Samples with 10 layers, 50 layers and 100 layers were made, and all showed reasonably similar effects. Unless specifically mentioned, all data represent measurements on separate samples.

Special care was used for the handling and storage of materials that show aging properties at room temperature. Samples with 10 layers took about two hours to make. As the number of multilayers increased to 50-100 layers, depositions could extend over several days. Aging presumably begins during the deposition process, but for these samples the aging at room temperature was quite slow, with a characteristic time estimated to be approximately 3 weeks for samples deposited at 35° C. Care was however taken to minimize any type of aging that may occur before the sample was actually measured. Once removed from the evaporation chamber the samples were placed in an argon glovebox where they were removed from the evaporation sample holder and separately placed in specimen holders in an argon environment. The samples were then stored at 77K. When needed a particular sample was removed, warmed to room temperature in a dry box and either placed directly into the apparatus for magnetoresistance measurements or attached to the sample holder with GE varnish for magnetization measurements. The varnish was allowed to dry for four hours before placing the sample in the LakeShore Model 7307 Vibrating Sample Magnetometer (VSM) with Magnetoresistance (MR) option.

The sample insertion and recording techniques for the magnetization and resistance measurements were slightly different. For the magnetization measurements, the cryostat was preheated to the measuring temperature and the magnetic field was set to 0 T. The sample and sample rod were placed in the cryostat, attached to the head drive, the head drive turned on and an initial zero field magnetization measurement was made. Here, there are some sample to sample deviations. For example, individual zero field magnetization measurements varied from −132 μemu to 300 μemu although most samples had zero-field magnetizations of a few μemu to a few tens of μemu. The largest measured values correspond to values of approximately 10-15% of the maximum magnetization (≈2.2-2.5 memu) obtained once the field is turned on. A 0.01 T magnetic field is then turned on and this sets time t=0 for the aging decay. Once the field is set there is a large rapid rise in the magnetization which maximizes in usually a few tens of seconds. The signal then begins to decay. During the magnetization decay the magnetization was measured every 10 seconds. The measurements reported here were made with both the magnetic field and sensing coils directed into the plane of the multilayers. The out-of-plane magnetic measurements show similar results but with a maximum magnetization of about 25% of the in-plane magnetization. The magnetic moments therefore appear to be directed mainly in-plane. Bulk Co is hexagonal and the easy direction is the c axis, as noted in A. H. Morrish, The Physical Principles of Magnetism, Wiley, New York 1965.

For the majority of resistance measurements the sample and MR probe were inserted into a cryostat, preheated to the measuring temperature and into a preset magnetic field of 0.01 T. Several resistance vs. time measurements were also made in zero magnetic field. Once the program was initiated it took approximately 130 s for the apparatus to take the first point. The measurements reported here are made with the Lakeshore MR Option which is a 4-probe method using 4 in-line tantalum leads to pierce through the multilayers. This geometry leads to the current flowing in-plane and we directed the magnetic field along the current direction. Two measurements (current parallel to, and 180° to the magnetic field) were made and averaged for each point.

After observing the aging decays we attempted to reinitialize the samples to determine if we were dealing with chemical or physical aging. Holding the sample (350° C. deposited) at 400K in 1 T for 24 hours did not reset the sample back to its initial condition. We also tried placing the samples (for short periods of time 10 s-60 s) into a preheated oven over a range of temperatures varying from 700K to 1100K. We were not able to reset the sample and began to conclude that chemical aging was likely.

We set out to eliminate the possibility that chemical aging occurs due to the substrate or due to oxygen annealing. Although solid-state dynamics are arguably too slow (in this temperature range) for Si in the substrate or oxygen (samples were open to air) to diffuse through the 10-250 multilayers in the samples we have made, it was considered. We should also add that either of these scenarios would likely increase the resistance not decrease it. Samples were produced on Si, $Al_2O_3$ and Al foil with similar and consistent decay effects observed. This appears to rule out the substrate as a major mechanism for the decay.

Oxygen could also modify the magnetic moments if it diffused into these thin film samples. Oxygen could enable antiferromagnetic coupling of the Co moments through the superexchange interaction. While we have not been able to rule this scenario out with magnetic experiments, a 100 nm Au cap was placed on a sample as a barrier to oxygen penetration before aging it and effectively the same aging behavior occurred. This rules out oxygen annealing during measurement as the mechanism for the decay. The other possibility is that oxygen combines with the Co during deposition in the vacuum chamber, although the level of the vacuum suggests that this should not be significant.

Nanoparticle Array in Matrix Material

We initially set out to produce nanoparticles of Co in a solid-state Sb matrix with growth formation through a Volmer-Weber growth mechanism. In an earlier study, we deposited samples at room temperature and gave significant time (5 min) after Co deposition to maximize nanoparticle growth. Every 5 multilayers the assembly was let cool for 30 minutes to maintain a deposition temperature of approximately room temperature.

We found in these samples magnetic signatures of 6-8 nm Co nanoparticles (Peak in ZFC, ZFC-FC remanence, 100K-200K blocking temperature, strong field dependence of peak, no waiting time effect), indicating that small Co particles were produced, and not perfect layers.

After aging, the nanoparticle signature disappeared. Low angle x-ray data showed no evidence of superlattice peaks corroborating the lack of ideal layering. Data on samples presented here were deposited on substrates held at 35° C. and 50° C. These samples showed a ferromagnetic signature as discussed above and no evidence of a blocking temperature (ZFCFC remnant, peak in ZFC magnetization). One distinct possibility considering the formation of nanoparticles is that single magnetic domain nanoparticles are forming at these raised deposition temperatures and these particles are responsible for the ferromagnetic signature.

However, there are other experimental approaches that can be used to form nanoparticle arrays within a matrix material.

Further Aspects, Including Applications and Devices

An aging sensor experiences a time and thermal environment similar to that of a monitored physical system of which it is part, or otherwise proximate. An advantage of nanoparticle-based aging sensors is that the characteristic aging parameters (such as time-temperature parameters, including a characteristic time) are readily controllable by adjusting e.g. the composition, size, shape, density, and/or configuration of the nanoparticles. This may be much simpler and/or versatile than trying to adjust the parameters of a bulk material or specific molecular compound.

Aging sensors allow improved safety, for example food may be okay if left outside the refrigerator, so long as the integrated aging is not above a monitored threshold. Typically expiry dates are based on time alone, and may wrongly indicate that food is not spoiled, even where the food has been mishandled and left out of the refrigerator. Indicators of temperature excursion may wrongly show that the food is spoiled even if the room temperature exposure is relatively short. The improved approach of the present invention allows the combination of time and temperature exposure to be more accurately monitored, giving a more accurate reading of whether food or other product has expired.

Example aging sensors include a solid-state structure that can be used to mimic, and hence determine, the aging properties of products, systems, and materials such as food items including dairy products, medical supplies, medical monitoring, chemicals (e.g. volatile chemicals), pathogen (e.g. bacterial) growth, electronic circuits such as semiconductor devices, mechanical components, structural components, materials, and the like. In some examples, the faster aging of hotter items can be monitored and determined using the electrical resistance and/or magnetization of a solid-state device. Other parameters, such as thermal resistance, specific heat, etc. may also be monitored. A distinct change in one or more parameters may be observed representing aging of the item of interest.

Example solid-state structures include nanoparticles and a matrix material. The nanoparticles may be magnetic nanoparticles, in particular ferromagnetic particles. Ferromagnetic nanoparticles may consist essentially of, or otherwise include one or more of the following: cobalt (Co), nickel (Ni), iron (Fe), manganese (Mn), or ferromagnetic rare earth material. Magnetic and electrical resistance may fall due to a variety of processes, such as nanoparticle melting, thermal demagnetization, etc. In some examples, magnetic nanoparticles may be formed in a magnetic multilayer device, for example a device including semimetal layers.

In some examples, magnetic and resistive properties of the structure are modified by the melting or other change in the form or state of the nanoparticles. For examples, the nanoparticles may initially be electrically isolated from each other, then melt into each other to provide a lower conductivity path through a matrix material. In such examples, the nanoparticles preferably have an electrical conductivity much greater than a surrounding or adjacent matrix material, for example one or more orders of magnitude greater. The structure may be used to monitor aging in the form of time-temperature combinations, or in some examples may be used to detect excursions above a certain threshold temperature.

Examples of the present invention include apparatus configured to provide a signal after a certain degree of aging has occurred. Aging in this context may correlate with the passage of time combined with one or more other parameters, such as temperature. For example, aging may relate to a time-temperature integration or other temperature modified time period. Aging may be related to an integration or other mathematical combination of a temperature excess beyond a threshold temperature and time, or other combination of physical parameter(s) and time.

An apparatus may include an electrical circuit responsive to a change in magnetization, resistance, or other parameter sensitive to the aging process. For example, an electronic circuit may be in electrical communication with a structure according to an example of the present invention and provide an electrical signal responsive to detected aging. In other examples, the electronic circuit may communicate with a transponder circuit including the structure, for example using capacitive or inductive RFID approaches. For example, a hand-held scanner may be used to interrogate the status of aging sensors on milk or other item.

An electronic circuit may provide a warning light, sound, or vibration in response to a detected degree of aging. An electronic display may be used to give a message. The change in conductivity in the structure may be used as a switch, and in some cases may be used as a fuse.

Aging may also be responsive to other conditions, such as pressure, humidity, presence of chemicals (such as oxidising agents), and the like. Some examples of the invention include devices responsive to such parameters. For example, external pressure or other mechanical force effects may induce reorientation, alignment, shape modification, and/or combination of nanoparticles, leading to a change in magnetic properties and/or resistance. For example, stretching of a component may be detected as nanoparticles are brought into contact with each other. Humidity may also influence the aging properties, and this may be detected in combination with time and/or temperature effects.

Examples of the present invention can be used to monitor a variety of systems or products, such as physical or chemical systems and a variety of commercial products. A solid-state structure, such as those described herein, may be included within the system (for example included within a system component), attached to a system component, or otherwise be exposed to similar conditions as the monitored system.

Monitored products may include food products, in particular perishable food products such as milk, other dairy products, meat, and the like. Aging may be monitored after packaging. In some cases, food processing may be monitored, e.g. to determine if a food product has been exposed to an excessive (or insufficient) combination of temperature and time during processing. This may help reduce the loss of nutrients during processing, or may be used to ensure sufficient sterilization.

Other monitored items may include medical supplies (such as pharmaceuticals), chemicals subject to aging degradation, and the like.

Other monitored items (such as physical systems) may include buildings, bridges, roads, other infrastructure, vehicles such as aircraft, and the like. For example, excessive forces in bridges or other dangerous excursions within component operating parameters may be detected, for example through an effect on the nanoparticles, such as local heating.

In some examples, a device may use a reversible effect, and may be reset e.g. using poling magnetic fields to restore ferromagnetic behavior of the nanoparticles. In some examples, the aging response may be non-reversible, in a single use device. The aging sensors may be cheap enough to be disposable, for example formed as a patch on a product to be monitored.

In some examples, the nanostructure, such as nanoparticles, have distinct shape anisotropy, having a dimension in one direction appreciably greater than dimension(s) in one or more orthogonal directions. The shape anisotropy, in the form of dimension ratios, may be greater than 2, for example greater than 5. The nanoparticles may be disks, flakes, rods, nanowires, and the like.

In some examples, the nanoparticles may be small enough to enhance melting under conditions of interest. For example, the nanoparticles may have a dimension (such as a diameter or equivalent thereof) in the range 0.1-10 nm, such as 0.5-5 nm, e.g. 1-2 nm. All ranges herein are inclusive, and in some examples may be approximate.

In some examples, the matrix material may be a semimetal or semiconductor such as arsenic (As), antimony (Sb), bismuth (Bi), tin (Sn), and the like, other semimetal, or combination or compound thereof. The nanostructure material may wet a matrix material surface on which it is deposited, facilitating the formation of flake-like nanoparticles that are much wider than they are thick.

In some examples, the matrix material may be a metal, preferably having an electrical conductivity appreciably less than that of the nanoparticle material. For example, a device may comprise magnetic nanoparticles and a relatively high resistance non-magnetic metal. Spin discontinuities at the nanoparticle interfaces increases the conductivity of the device. However, as nanoparticles either demagnetize or fuse together, the conductivity of the electrical path is reduced. This may be detected, and the degree of resistance (or magnetization) reduction can be used as an estimate of system aging.

In some examples, the nanostructures may be non-magnetic, and the matrix material may be a semimetal or relatively high resistivity metal. For example, copper, gold, silver etc. nanostructures may be formed in a tin, antimony etc. matrix. As the low resistivity nanoparticles fuse together, a lower conductivity path is formed which may then be electrically detected.

In some examples, the matrix material may be a semiconductor, e.g. with band discontinuities at the nanoparticle-matrix boundaries providing an impediment to electron or hole transport. In some examples, the matrix material may be or include a metalloid, such as boron, germanium, silicon, arsenic, antimony, or tellurium. In some examples, the matrix material may be a polymer and/or a flexible material, e.g. that may be conformed to a surface, stretched, etc.

The structure may be a multilayer structure, for example including one or more matrix material layers alternating with one or more nanoparticle layers. In some examples, nanoparticles may be dispersed through a matrix material, e.g. in the form of a composite.

Patents, patent applications, or publications mentioned in this specification are incorporated herein by reference to the same extent as if each individual document was specifically and individually indicated to be incorporated by reference. In particular, U.S. Provisional Application 61/476,044, filed Apr. 15, 2011, is incorporated herein by reference.

It is appreciated that a suitable time-temperature indicator for passive RFID cold chain applications demands several properties. In particular, the indicator must have well defined time-temperature characteristics that span both necessary time and temperature regimes such as minutes to months for temperatures ranging between approximately 50° C. to −10° C. In addition, such time-temperature properties should be apparent within the solid-state structure and be driven by thermal energy of surrounding heat such that an onboard power supply is not needed. Furthermore, such a passive RFID sensor must be able to be probed at lower powers, e.g. <20 µW. Naturally, such a sensor should be inexpensive to produce. In order to better teach the invention but not limit its scope in any manner, examples of such a sensor that was developed for the aging of milk are described below.

Additional multilayer samples were prepared in an Edwards E306A e-beam evaporator with a starting pressure of $2\times10^{-7}$ torr. Also, samples were deposited on a substrate face of <100> silicon held at a temperature of 50° C. It is appreciated that previous measurements have shown that similar time-temperature results can be obtained on other substrates, e.g. Mylar film, glass etc.

Co/Sb multilayer samples with Co layer thicknesses of 1.5 nm, 1.0 nm and 0.8 nm were produced. All the samples had Sb layer thicknesses of 2.5 nm. In addition, an initial 2.5 nm layer of Sb was deposited on the bare substrate followed by the layer of Co. This was repeated 10 times and the sample was capped with a final 2.5 nm layer of Sb. After deposition, the master sample was removed from the chamber and stored in liquid nitrogen to effectively stop thermal aging. To prepare a sample for a resistance measurement, the master sample was removed from liquid nitrogen and brought to room temperature in a desiccator to prevent water formation. An approximately 4 mm×4 mm sample was cut for the measurement and the master sample placed back into the liquid nitrogen.

All resistance measurements were conducted using a MagnetoResistance (MR) probe option on a LakeShore Model 7307 Vibrating Sample Magnetometer (VSM). After loading a sample onto the MR probe and measuring the room temperature resistance, the sample was inserted into the cryostat which had been preheated to a desired measuring temperature. All resistance measurements in this study were made with a direct current (dc) technique. Measurements were conducted with both 2-probe and 4-probe dc resistance techniques. The 4-probe technique is an in-line measurement with current leads set 3 mm apart, and voltage leads separated by 1 mm and located in-line 1 mm from the respective current leads. The 2-probe measurement sensed the voltage drop across the current leads. The 2-probe measurement therefore measured a voltage drop across 3 mm of sample as opposed to 1 mm in the 4-probe measurements.

Resistance decay results for the Co/Sb (1.5 nm/2.5 nm) and Co/Sb (1.0 nm/2.5 nm) samples were made with the 4-probe technique. The resistance decay results for the Co/Sb (0.8 nm/2.5 nm) samples were made with the 2-probe technique. Both 2-probe and 4-probe measurements were made on the Co/Sb (1.5 nm/2.5 nm) samples for a comparison therebetween. Finally, for the resistance vs. temperature measurements a 10 layer Co/Sb (1.0 nm/2.0 nm) sample was produced.

Variations in sample size produced notable changes in the initial room temperature resistance. In the 2-probe measurements, small samples (2 mm×4 mm) had initial room temperature resistances as large as 700Ω. Large cut samples 5 mm×6 mm had much smaller initial resistances on the order of 200Ω. The standard 4 mm×4 mm had initial room temperature resistances of 380±20Ω. Also, 4-probe measurements produced resistances approximately an order of magnitude smaller.

In general, for the first 7 to 10,000 seconds a resistance measurement was taken every 200 seconds. However, for very long time measurements that extend out to approximately two weeks, a measurement was taken every hour or every three hours for times longer than 7000 seconds. All resistances were measured in zero magnetic field.

Figure 10:
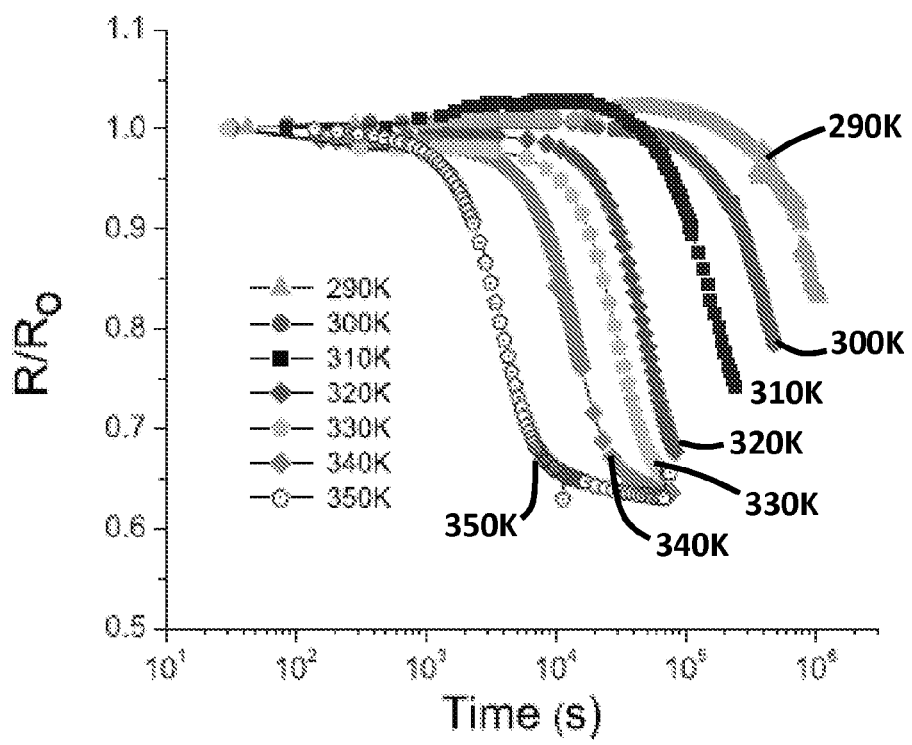
FIG. 10 is a graphical plot illustrating decay of normalized resistance as a function of log time for Co/Sb (0.8 nm/2.5 nm) samples with decays measured at temperatures ranging between 290 K (16.85° C.) to 350 K (76.85° C.)

FIG. 10 shows a complete set of resistance versus time decay curves for Co/Sb (0.8 nm/2.5 nm) sample with temperatures ranging from 290 K to 350K. As observed in the figure, the sample ages more rapidly at higher temperatures. The resistance decay process is irreversible so each curve corresponds to a different sample cut from a master sample. In each sample the resistance decays from its initial resistance value of $R_o$ to a final resistance of approximately $0.6\ R_o$. The final resistance ratio $R/R_o \sim 0.6$ for samples with a Co thickness of 0.8 nm is similar to the final resistance ratios of 1 nm Co samples that exhibit a $R/R_o \sim 0.6$ and greater than the 1.5 nm Co samples that exhibit a $R/R_o \sim 0.5$.

Figure 11:
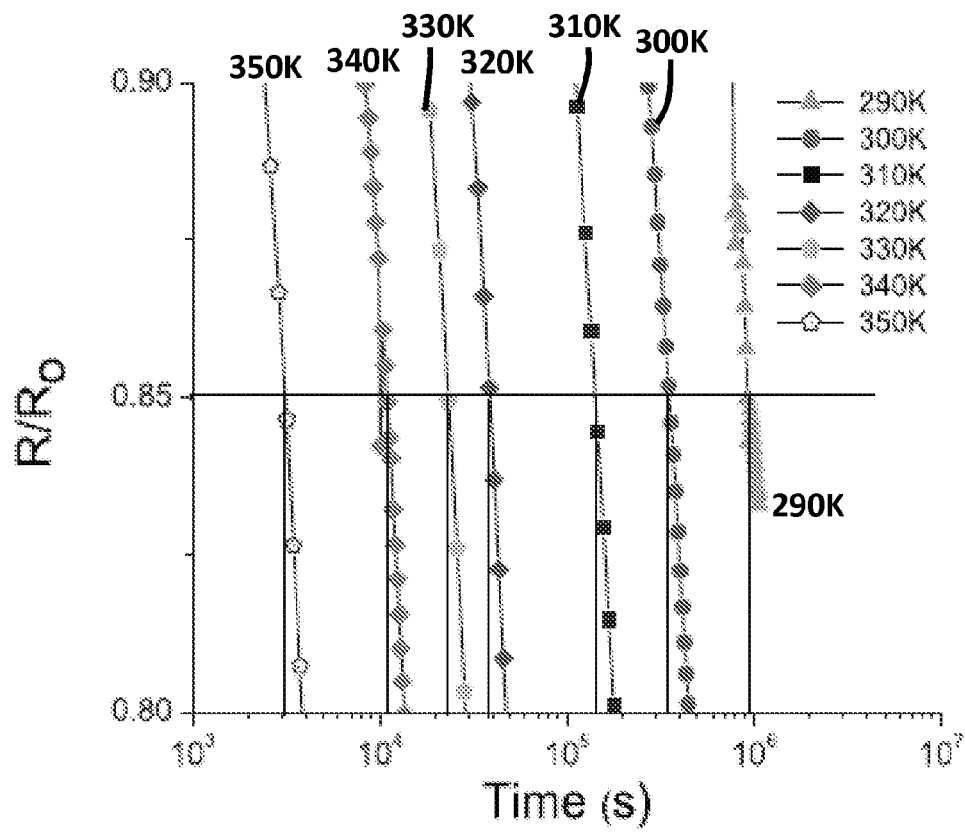
FIG. 11 is a graphical plot illustrating a magnified or enlarged portion of FIG. 10 for resistance ranges between 0.8 $R_o$ to 0.9 $R_o$.

For the Co/Sb multilayer samples with Co layer thicknesses of 1.5 nm and 1.0 nm, the inflection point of the decay curves was plotted on a log scale to determine a characteristic timescale τ for each individual decay curve. It is appreciated that this type of analysis is common in the analysis of aging curves. It is also appreciated that the inflection point is a natural place for determining a characteristic timescale as it is a peak in the logarithmic derivative function $S(t)=dM_{TRM}(t, t_w)/d\ln t$ and for a continuous set of measurements such a timescale is beneficial. In the alternative, if a sample is probed intermittently, such as in RFID detection along a supply chain, there may not be enough data to make a full decay plot or a logarithmic derivative plot. Therefore, and in order to simplify this analysis for the Co/Sb (0.8 nm/2.5 nm), a time scale associated with a resistance value of $0.85\ R_o$ was acquired as illustrated in FIG. 11. It is appreciated that the value of $0.85\ R_o$ is a little larger than the inflection point for all of the curves generated. Also, such a graph as shown in FIG. 11 affords extraction of a timescale associated with the value of each individual resistance curve at $0.85\ R_o$. While simplifying this analysis to extract a single timescale is useful for Arrhenius law fitting, this technique does not preclude systematic or intermittent measurements of the decay for more detailed analysis.

In FIG. 10 the resistance versus time plots are plotted on a log scale within which it may be difficult to appreciate the wide range of time scales spanned for the temperature range. Values of temperature (K) versus τ (sec) are shown in Table 1 below. In particular, at 350 K the time to decay to $0.85\ R_o$ is $3.04\times10^3$ seconds or about 50 minutes. At 320 K the time to decay to $0.85\ R_o$ is $3.9\times10^4$ seconds or about 11 hours and at 290 K the time to decay to $0.85\ R_o$ is $8.9\times10^5$ seconds or about 10.3 days.

TABLE 1

Values of the characteristic time τ (timescale at .85 R/$R_o$) as a function of temperature for Co/Sb (0.8 nm/2.5 nm).

| Temp (K) | T (sec.) |
| --- | --- |
| 290 | $8.9\times10^5$ |
| 300 | $3.3\times10^5$ |
| 310 | $1.3\times10^5$ |
| 320 | $3.9\times10^4$ |
| 330 | $2.2\times10^4$ |

TABLE 1-continued

Values of the characteristic time τ (timescale at .85 R/R$_o$) as a function of temperature for Co/Sb (0.8 nm/2.5 nm).

| Temp (K) | T (sec.) |
|---|---|
| 340 | 1.05 × 10$^4$ |
| 350 | 3.04 × 10$^3$ |

The time and temperature dependence of the decays in these samples indicate that the process is thermally activated. Also, it is appreciated that when a system in one state can transition to another state by thermally activated hopping over an energy barrier, the system can generally be described by an Arrhenius law.

In chemical reactions the Arrhenius law is often written as the rate equation:

$$k = Ae\frac{-E_a}{RT} \quad (2)$$

where k is the reaction rate $E_a$ is the activation energy, R is the ideal gas constant, T is the temperature in Kelvin and 'A' is the frequency factor that gives the rate for zero activation energy for infinite temperature. In a chemical reaction, the activation energy is the energy needed to overcome the energy barrier that separates an initial chemical state from some final chemical state.

For a time-temperature analysis disclosed herein, the time dependence for the state transition given by the Neel-Arrhenius of equation (1) was used. Also, in order to account for a chemical reaction analysis of food products, the ideal gas constant was used and data for a straight line on a ln(τ) vs. 1/T plot was used per the equation;

$$\ln(\tau) = \frac{E_a}{R}\left(\frac{1}{T}\right) + \ln(\tau_o) \quad (3)$$

Figure 12:
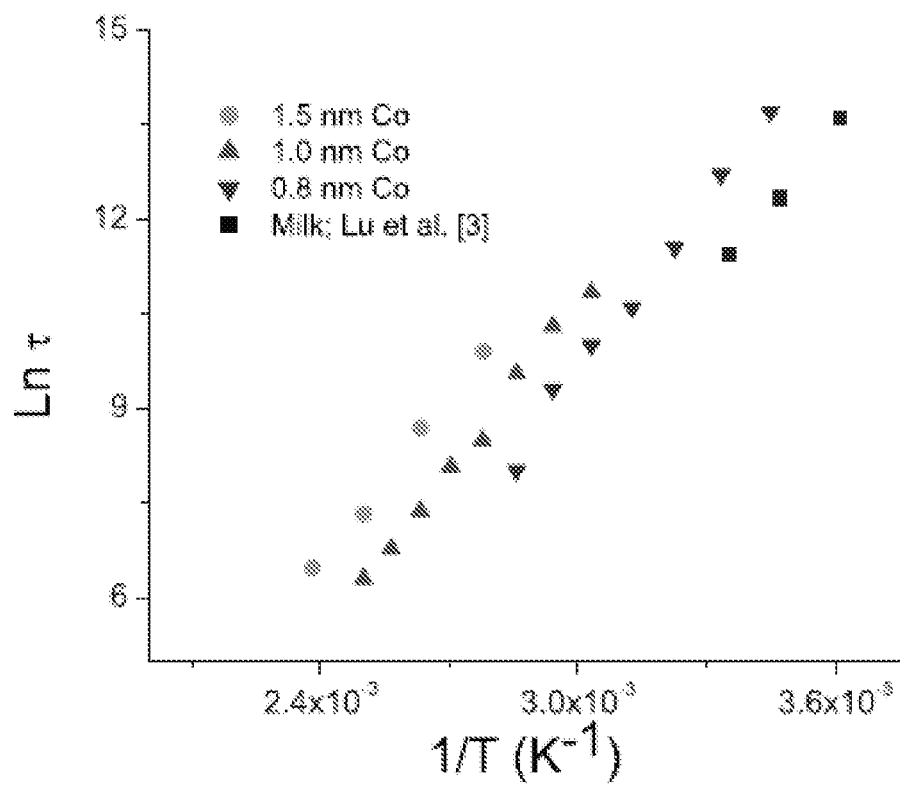
FIG. 12 is a graphical plot of $\ln(\tau)$ versus 1/T for three Co/Sb samples and milk.
Figure 13:
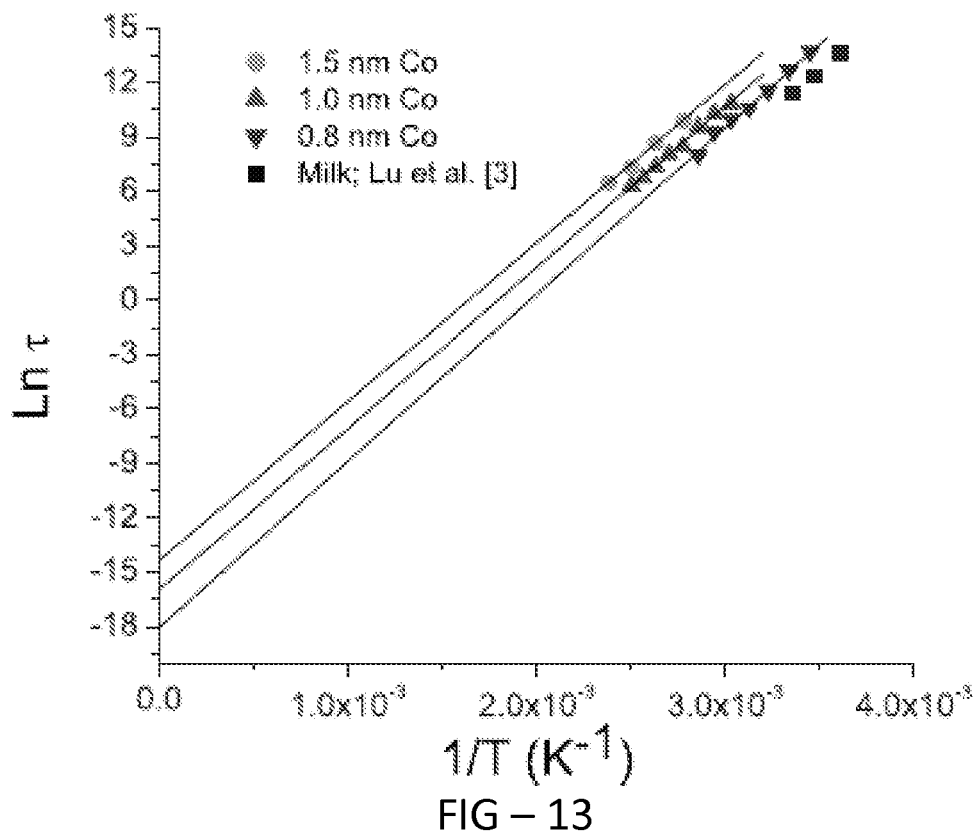
FIG. 13 is a graphical plot illustrating the same data shown in FIG. 12 but on an expanded scale and with straight lines illustrating the Arrhenius law fit to the data.

Turning now to FIG. 12, a graph of ln(τ) vs. 1/T for three Co/Sb samples plus data for milk is shown. FIG. 13 illustrates straight line fits to the activation energy extrapolated to 1/T=0 K$^{-1}$, T=∞. The y-intercept on this graph gives the fluctuation time scale $\tau_o$.

Table 2 below shows the values of the activation energy $E_A$ for three Co/Sb runs (varying thickness) and the fit parameter for the milk data. Table 2 also displays the fluctuation timescales $\tau_o$ for the four samples. It is clear from FIG. 12 (slopes of the lines) and from Table 2 that all four samples have reasonably similar activation energies. After observing the activation energies and fluctuation timescales ($\tau_o$) for the Co/Sb (1.5 nm/2.5 nm) and Co/Sb (1.0 nm/2.5 nm) samples, the Co/Sb (0.8 nm/2.5 nm) sample was chosen to make a milk sensor for the following reasons. First, the Co/Sb (0.8 nm/2.5 nm) sample had activation energies similar to milk. Second, the time-temperature characteristics shifted towards the milk curve with decreasing Co thickness. In particular $\tau_o$ decreases as the Co thickness decreases and a further shift would approximate timescales of milk. Also, while $\tau_o$ did shift down, as expected, and $E_a$ varied a little, it is appreciated that while the Co/Sb (0.8 nm/2.5 nm) data is the closet to the milk data, it still does not overlap. As such, samples with smaller thicknesses of Co are thought to produce a perfect overlap.

TABLE 2

Values of the activation energy $E_a$ and the fluctuation time scale $\tau_o$ for three Co/Sb samples and milk

| Sample | $E_a$(kJ/mol) | $\tau_o$(s) |
|---|---|---|
| Co/Sb (1.5 nm/2.5 nm) | 73.1 | 4.85 × 10$^{-7}$ |
| Co/Sb (1.0 nm/2.5 nm) | 73.9 | 1.13 × 10$^{-7}$ |
| Co/Sb (0.8 nm/2.5 nm) | 76.6 | 1.42 × 10$^{-8}$ |
| Milk [7] | 78.4 | 9.89 × 10$^{-9}$ |

The reproducibility of the resistance decays of the Co/Sb (1.5 nm/2.5 nm) sample at a single temperature, 360 K was analyzed. Using the 4-probe measuring system described above, deviation in both the structures of the decay curves and in the characteristic timescale defined by the inflection point was observed.

Figure 14:
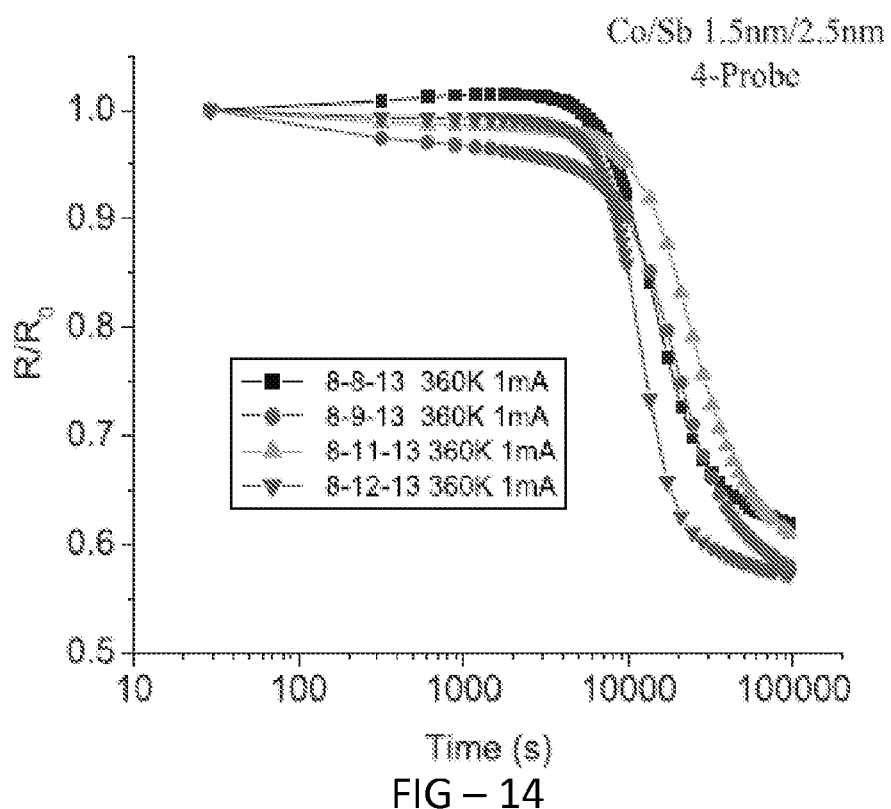
FIG. 14 is a graphical plot for a 4-probe resistance decay curve on four separate Co/Sb samples.
Figure 15:
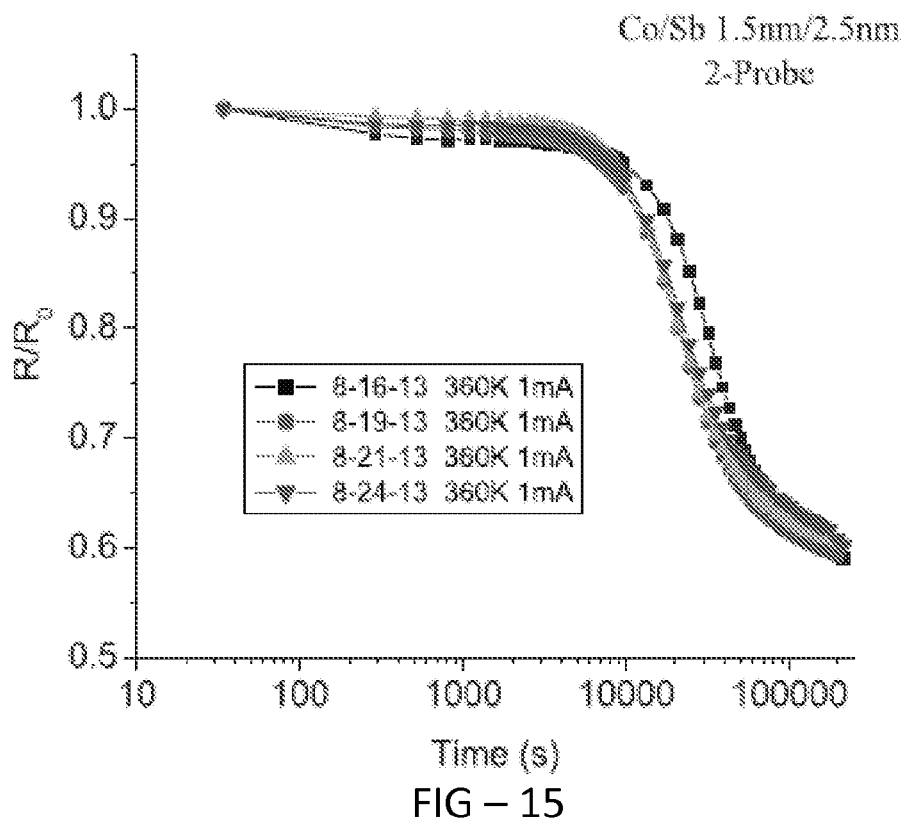
FIG. 15 is a graphical plot of 2-probe resistance decay curves on four separate Co/Sb samples.

Turning now to FIG. 14, resistance aging decay curves for the Co/Sb samples using the 4-probe technique are shown while FIG. 15 illustrates resistance aging decay curves for the Co/Sb samples using the 2-probe technique.

A simple model where the Co/Sb multilayer system can be thought of as two resistors in parallel has been previously developed and disclosed in J. Appl. Phys. 110, 114312 (2011). In particular one resistor consists of the antimony layers. Antimony is a semimetal and has a bulk resistivity of 417 nΩm, almost seven times higher than that of Co 62.4 nΩm. The second resistor is initially composed of the cobalt nanoparticles. This contribution to the initial resistivity of the sample is very high. While the resistance of cobalt is much lower than antimony, electrical current would not only need to transit through the nanoparticles, it would also need to transit through the highly resistant barrier between the magnetic cobalt nanoparticles and the antimony, as well as transit through the antimony going from one nanoparticle to another. As the nanoparticles coalesce, the cobalt acts as a short through larger and larger regions of the antimony. Therefore, one can envision the resistor corresponding to the cobalt resistance decreasing as a function of time. While this simple model can explain the resistance and magnetization decays the resistance versus temperature data of FIG. 16 suggest that the mechanism may be more complex.

Figure 16:
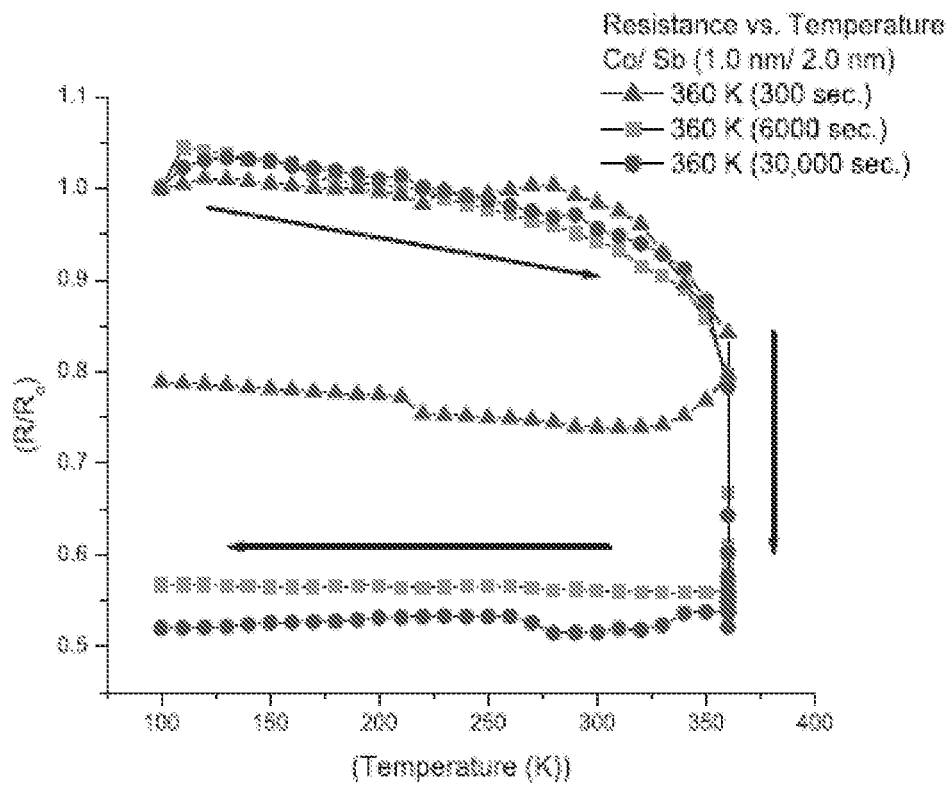
FIG. 16 is a graphical plot of temperature versus resistance for three Co/Sb samples.

For example, the data of FIG. 16 imply that during the aging decay, the samples may undergo a Metal-Non-Metal (MNM) transition. It is appreciated that such a transition could be an important result for RFID implementation as described later. Also, FIG. 16 illustrates resistance versus temperature results for a temperature cycle experiment in which un-aged samples were removed from storage at 77 K, loaded onto the MR probe, inserted into the cryostat and precooled to 100 K. From 100 K the temperature was increased and resistance measurements made every 10 K up to 360 K. The resistance versus temperature in the initial ramp from 100 K to 300 K displays a negative slope (−|dR/dT|) and is suggestive of semiconductor behavior. At 360 K, the three samples were aged for three different times, 300, 6000 and 30,000 sec. The temperature was then decreased to 100 K with resistance measurements taken at 10K intervals. As the time aged at 360 K increases the amplitude of the negative slope (−|dR/dT|) decreases. Finally, for the longest aging time (30,000 sec.) the sample has transitioned to a positive slope (+|dR/dT|) implying metallic behavior. At 30,000 seconds of aging, this sample is fully aged as determined from a measured resistance decay curve.

Antimony is a semi-metal with a long history of being utilized in semiconductor technology particularly as GaSb and AlSb. Also, kieftite (CoSb$_3$), is a well known diamagnetic semiconductor. At first glance, looking at the resistance versus temperature graph of FIG. 16, and considering possible alloying during thin film deposition one might surmise that $CoSb_3$, a semiconductor, is formed on deposition and perhaps separates into Co and Sb during the aging process, producing a metal. However, this view is contradicted by STM, AFM, MFM and SEM scans which show nanoparticle formation upon deposition and MFM scans which show evidence of single magnetic domain magnetic nanoparticles in un-aged samples. Also, magnetization versus temperature curves display a blocking temperature of ≈100 K which is indicative of superparamagnetism and suggests formation of magnetic nanoparticles on deposition. Finally the magnetic aging signature including an approximately 80% reduction in sample magnetization, eliminates phase separation of $CoSb_3$ as a mechanism for aging. An opposing diffusion model where Sb diffuses into Co nanoparticles or Co atoms into the Sb to form $CoSb_3$ might explain the aging decays of the magnetization but would likely increase the resistance and would be at odds with the data of FIG. 16.

Not being bound by theory, the negative dR/dT for the un-aged or slightly aged samples observed in FIG. 16, is due to the Sb layers (2.0 nm layers, 20 nm total Sb thickness) being under the influence of strong magnetic fields exerted locally by the magnetic nanoparticles. As such, when the magnetization decreases, this effect also decreases.

There are several issues to be addressed in implementing these sensors in an RFID transponder. A preliminary issue is the presentation of the decay data as a function of $R/R_o$. We cut our samples by hand with a diamond scribe and get variations in sample sizes. As previously mentioned size variations can give significant initial resistance variations without changing the time-temperature dependence. Therefore it is likely that by implementing a consistent geometry in the sensors, absolute resistances will suffice. A second solution would be to store $R_o$ on initialization of the sensor then feeding back both the initial resistance and the resistance at read time to the reader for further processing.

Figure 17:
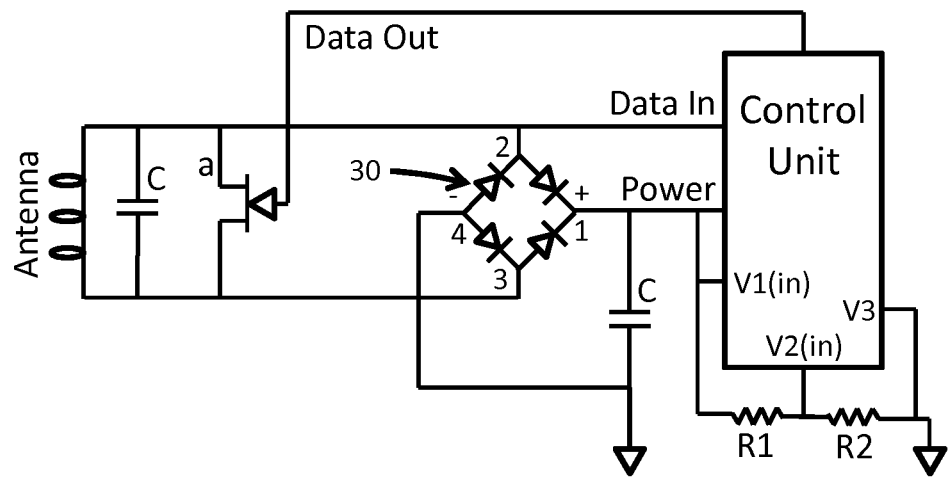
FIG. 17 is an illustration of an RFID sensor according to an embodiment of the present invention.

A plausible DC configuration within an RFID circuit might include rectification of the input signal coupled through the Co/Sb sample in series with a known resistance as illustrated in FIG. 17. A measurement of the voltage drop across the known resistance would determine the current through the Co/Sb sample and a measurement of the voltage drop across the Co/Sb sample would, coupled with the current, provide a determination of the sample resistance. These two values could be stored and sent to the reader for further processing.

With knowledge of the initial resistance, an in situ resistance reading, and a measurement of the ambient temperature, a good estimation of the shelf life can be obtained from fitted curves. Good fits to the data with sigmoidal functions have been obtained. In general, sigmoidal function fitting of individual decay curves has been used as a prelude to taking the logarithmic derivative in order to obtain an S(t) function and τ from the maximum in that function. Since the RFID application does not require taking a derivative, it is possible that a polynomial fit would suffice. For accurate shelf life readings, for any temperature, a universal sigmoidal/polynomial function is developed which can fit the two resistance points mentioned above for any ambient temperature thereby providing an extrapolated estimate of shelf life at that temperature.

It is appreciated that the matrix material can be metallic in nature and preferably semiconductor in nature. The nanoparticles of the nanostructures can be spherical, ellipsoidal, cylindrical, pancake-shaped, rectangular-shaped, square and/or cube-shaped and the like. In addition, the magnetic nanoparticles are single magnetic domain nanoparticles, i.e. each of the nanoparticles contains a single magnetic domain. As discussed above, the magnetization of the nanostructures decreases as a function of time. Not being bound by theory, migration of the nanoparticles into contact with each other results in the formation of multi-domain structures which reduce the external magnetic field. Such multi-domain structures can be one-dimensional nanowires, two-dimensional agglomerations within a plane, or three-dimensional agglomerations. Interaction of the nanoparticles with the matrix through local diffusion, melting, etc. reduces the magnetism of the individual nanoparticles by rearranging the atomic magnetic moments in the magnetic domain. In addition, it is appreciated that the reduction in magnetization can be due to diffusion the Sb into the Co and/or vice versa forming alloys.

The decrease in magnetization is accompanied by a decrease in the resistivity of the sample and the reduced resistivity can be due to low resistance channels formed by or through the agglomerated nanoparticles. However, the reduction in resistivity can be due to metal to non-metal transition (MNM) in the semi-metallic matrix.

The solid-state structure can exhibit capacitive changes during aging and monitor signals that monitor the age of the sensor and thus the food item could include monitoring the resonant frequency, the signal amplitude, and the phase difference between in-phase and out-of-phase responses. Furthermore, the MNM transition can be due to the effect of the reduction of local magnetization of the aged nanoparticles on the semi-metallic matrix.

The present invention also affords for a sensor or transponder that is without ID logic. For example, a simple LCR circuit can serve as a standalone radio frequency time-temperature indicator (RFTTI). As noted above, the time and temperature dependent reduction of the magnetization and resistivity follows Arrhenius law behavior and thus provides for a suitable time-temperature mapping.

Referring to FIG. 17, a schematic illustration of an RFID sensor is shown generally at reference numeral 30. Upon rectification of input power by a rectifier 300, current is sent through a known resistance R1 and then through the solid-state structure having a resistance or aging resistance R2. Voltages are recorded prior to input through resistance R1 (V1 (in)), after the current travels through R1 (V2 (in)), and finally after the current passes through R2 (V3). All three voltages are sent to the RFID reader, and with the voltage difference between V1 and V2, along with knowledge of R1, a value of current that passed through the aging resistor R2 is provided. Furthermore, the voltage difference between V2 and V3, coupled with knowledge of current, provides a value of the aging resistance R2. In this manner, the resistance of the solid-state structure can be measured and communicated with an RFID reader.

Figure 18:
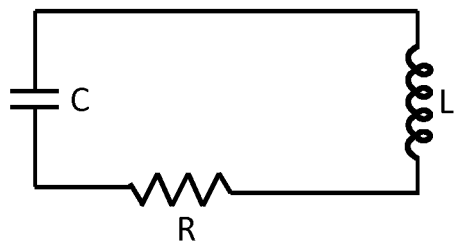
FIG. 18 is a graphical illustration of a simple series LCR circuit according to an embodiment of the present invention.

Referring now to FIG. 18, the solid-state nanoparticle structure can be used as the resistance/resistor R in a simple series LCR circuit such as one used as a resonant circuit within an RFID device or a standalone RFTTI device. The aging resistor R is placed in a simple series configuration and the reduction of the aging resistance is monitored from a change in the amplitude of the resonance signal due to the resistance change. Stated differently, a change in the damping factor $$\zeta = \frac{R}{2}\sqrt{\frac{C}{L}}$$

allows for measurement of amplitude change.

Figure 19:
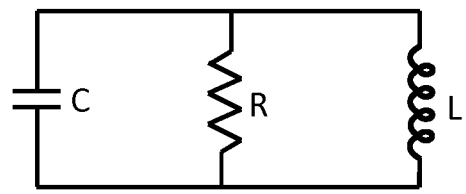
FIG. 19 is an illustration of a simple parallel LCR circuit according to an embodiment of the present invention.

A similar device is shown in FIG. 19 where the solid-state nanoparticle structure is placed as a resistance/resistor R in a simple parallel LCR circuit such as those used as a resonant circuit within an RFID device or a standalone RFTTI device. As shown in the figure, the aging resistor R is placed in a simple parallel configuration and the reduction of the aging resistor is monitored from a change in the amplitude of the resonance signal via a change in the damping factor $$\zeta = \frac{1}{2R}\sqrt{\frac{L}{C}}.$$

Figure 20:
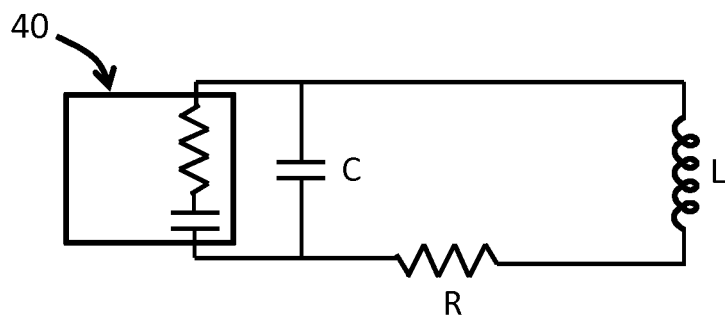
FIG. 20 is an illustration of a simple parallel resonant circuit according to an embodiment of the present invention.
Figure 21:
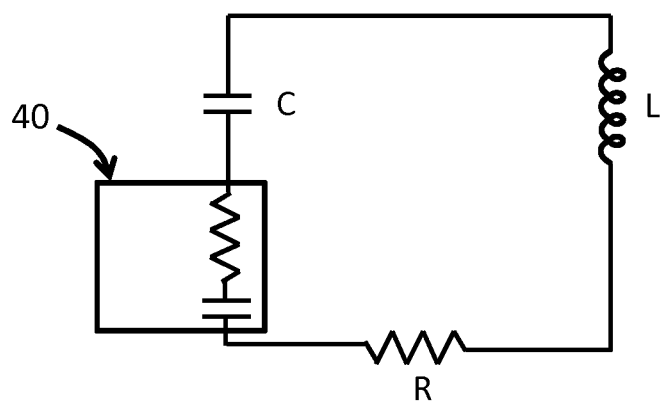
FIG. 21 is an illustration of a simple series resonant circuit according to an embodiment of the present invention.

With reference to FIGS. 20 and 21, capacitive anomalies associated with MNM transitions afford for the solid-state structure 40 to be coupled to or coupled within an LCR circuit. In particular, FIG. 20 illustrates a simple series LCR circuit with a traditional capacitor, resistor, and inductance unit. Coupled to this circuit is a solid-state structure in parallel with the capacitor. In the alternative, FIG. 21 illustrates the solid-state nanoparticle structure coupled in series with the capacitor C.

In addition to a change in resistance and capacitance values, it is appreciated that a dielectric constant and/or permittivity of an inventive device can change with aging. Therefore, the change of the dielectric constant and/or permittivity can be coupled with an RFID antenna and used and/or communicated to an RFID reader.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art.

I claim:

1. An RFID food item aging apparatus, said apparatus comprising: a solid-state structure having a plurality of ferromagnetic nanoparticles of a first material distributed in a matrix second material, said matrix second material being a semimetal or a semiconductor and magnetic interactions between neighboring nanoparticles resulting in temperature and time dependent electrical resistance and magnetization of the solid-state structure; said solid-state structure also having a first measurable value of electrical resistance and magnetization at a first time and a second measurable value of electrical resistance and magnetization at a second time said second measurable value of electrical resistance and magnetization being a function of a temperature profile of said solid-state structure between said first time and said second time; and an antenna in communication with said solid-state structure, said antenna operable to broadcast at least one of said first measurable value and said second measurable value of electrical resistance and magnetization to an RFID reader.

2. The apparatus of claim 1, wherein said solid state structure has a first morphological shape at said first time and a second morphological shape at said second time.

3. The apparatus of claim 2, wherein in said first morphological shape is a multilayer structure with at least one layer of said plurality of ferromagnetic nanoparticles between layers of said matrix second material.

4. The apparatus of claim 3, wherein said plurality of ferromagnetic nanoparticles have a first physical size in said first morphological shape and a second physical size in said second morphological shape, said second physical size being greater than said first physical size.

5. The apparatus of claim 4, wherein said plurality of ferromagnetic nanoparticles having said first physical size are single magnetic domain nanostructures.

6. The apparatus of claim 5, wherein said plurality of ferromagnetic nanoparticles grow from said first physical size to said second physical size by at least one of diffusion between said plurality of ferromagnetic nanoparticles and melting of at least a portion of said plurality of ferromagnetic nanoparticles.

7. The apparatus of claim 6, wherein said first physical size is in the form of elliptical-shaped ferromagnetic nanoparticles and said second physical size is in the form of nanowires.

8. The apparatus of claim 6, further comprising a pair of electrodes in electrical contact with said solid state structure, said pair of electrodes configured to determine said first measurable value of electrical resistance and magnetization at said first time and said second measurable value of electrical resistance and magnetization at said second time.

9. The apparatus of claim 8, wherein said pair of electrodes are configured to determine said first and second measurable values parallel to said layers of said multilayer structure.

10. The apparatus of claim 8, wherein said pair of electrodes are configured to determine said first and second measurable values perpendicular to said layers of said multilayer structure.

11. The apparatus of claim 1, wherein said second measurable value is less than said first measurable value due to a semimetal or a semiconductor to metal transition of said matrix.

12. The apparatus of claim 11, wherein said plurality of ferromagnetic nanoparticles have a first physical size at said first time and a larger second physical size at said second time, said plurality of ferromagnetic nanoparticles with said second larger physical size having a reduced local magnetization compared to said plurality of ferromagnetic nanoparticles with said first physical size.

13. The apparatus of claim 12, wherein said semimetal or a semiconductor to metal transition of said matrix is a function of said reduced local magnetization of said plurality of ferromagnetic nanoparticles with said second larger physical size.

14. The apparatus of claim 13, further comprising an LCR circuit, said multilayer structure being a resistor in said LCR circuit.

15. The apparatus of claim 14, wherein said LCR circuit with said multilayer structure is a stand-alone Radio Frequency Time Temperature Indicator.

16. The apparatus of claim 15, wherein said LCR circuit is a series LCR circuit.

17. The apparatus of claim 15, wherein said LCR circuit is a parallel LCR circuit.

* * * * *